(12) United States Patent
Denkewicz, Jr. et al.

(10) Patent No.: US 10,934,184 B2
(45) Date of Patent: Mar. 2, 2021

(54) SYSTEMS AND METHODS FOR SANITIZING POOL AND SPA WATER

(71) Applicant: Hayward Industries, Inc., Berkeley Heights, NJ (US)

(72) Inventors: Raymond P. Denkewicz, Jr., East Greenwich, RI (US); Arthur W. Johnson, III, Stoughton, MA (US); James Murdock, Wakefield, RI (US); James Carter, Warren, RI (US)

(73) Assignee: Hayward Industries, Inc., Berkeley Heights, NJ (US)

( * ) Notice: Subject to any disclaimer, the term of this patent is extended or adjusted under 35 U.S.C. 154(b) by 133 days.

(21) Appl. No.: 15/927,412

(22) Filed: Mar. 21, 2018

(65) Prior Publication Data

US 2018/0273404 A1    Sep. 27, 2018

Related U.S. Application Data

(60) Provisional application No. 62/474,333, filed on Mar. 21, 2017.

(51) Int. Cl.
*C02F 1/467* (2006.01)
*G01N 33/00* (2006.01)
(Continued)

(52) U.S. Cl.
CPC ............ *C02F 1/4674* (2013.01); *B64C 39/02* (2013.01); *G01N 33/0052* (2013.01);
(Continued)

(58) Field of Classification Search
CPC ..... B64C 39/00; B64C 39/02; B64C 2201/00; B64C 2201/12; C02F 1/00; C02F 1/30;
(Continued)

(56) References Cited

U.S. PATENT DOCUMENTS

D138,325 S    7/1944  Pool
2,436,077 A   2/1948  Robertson
(Continued)

FOREIGN PATENT DOCUMENTS

CN    2188767 Y    2/1995
CN    1147435 C    4/2004
(Continued)

OTHER PUBLICATIONS

International Search Report of the International Searching Authority dated Jul. 5, 2018, issued in connection with International Application No. PCT/US18/23514 (5 pages).
(Continued)

*Primary Examiner* — Natasha E Young
(74) *Attorney, Agent, or Firm* — McCarter & English, LLP

(57) ABSTRACT

Systems and methods for sanitizing pool/spa water are provided. An electrolytic chlorinator is provided which includes a combined flow, temperature, and salt concentration sensor. The electrolytic chlorinator could include an acid tank for in-situ cleaning of the electrolytic chlorinator or acidification of pool/spa water where needed. A delayed polarity reversal technique is provided for de-scaling and managing passivation of the blades of an electrolytic chlorinator. The electrolytic chlorinator could include a sacrificial anode for protecting components of the chlorinator as well as other pool/spa components. The electrolytic chlorinator could include an integral, electrically-controlled acid generator, a brine tank for periodically superchlorinating and/or shocking pool/spa water, and/or a plurality of chemical tanks/feeds for periodically injecting chemicals into the chlorinator. A combined ultraviolet (UV)/Ozone and salt (electrolytic) chlorine generator is provided, as well as: filters having integral UV sanitizers; reflective linings for
(Continued)

UV sanitization systems; means for injecting bubbles into pool/spa water.

17 Claims, 17 Drawing Sheets

(51) Int. Cl.
*G01N 33/18* (2006.01)
*B64C 39/02* (2006.01)
*C02F 103/42* (2006.01)
*C02F 1/461* (2006.01)
*C02F 1/78* (2006.01)
*C02F 1/32* (2006.01)

(52) U.S. Cl.
CPC ........ *G01N 33/182* (2013.01); *B64C 2201/12* (2013.01); *C02F 1/325* (2013.01); *C02F 1/78* (2013.01); *C02F 2001/46119* (2013.01); *C02F 2103/42* (2013.01); *Y02W 10/37* (2015.05)

(58) Field of Classification Search
CPC .... C02F 1/32; C02F 1/325; C02F 1/46; C02F 1/461; C02F 1/46104; C02F 1/46109; C02F 1/467; C02F 1/4672; C02F 1/4674; C02F 1/72; C02F 1/78; C02F 2001/46119; C02F 2103/00; C02F 2103/42; G01N 33/00; G01N 33/0004; G01N 33/0009; G01N 33/0027; G01N 33/0036; G01N 33/0052; G01N 33/18; G01N 33/182; Y02W 10/00; Y02W 10/30; Y02W 10/37
See application file for complete search history.

(56) References Cited

U.S. PATENT DOCUMENTS

| | | |
|---|---|---|
| 2,644,700 A | 7/1953 | Woodling |
| 3,079,498 A | 2/1963 | Ruffin |
| 3,162,470 A | 12/1964 | Davidson et al. |
| 3,336,099 A | 8/1967 | Czulak et al. |
| 3,632,498 A | 1/1972 | Beer |
| 3,803,573 A | 4/1974 | Schonger |
| 3,929,151 A | 12/1975 | Rubin |
| 3,933,616 A | 1/1976 | Beer |
| D242,618 S | 12/1976 | Milo |
| 4,100,052 A | 7/1978 | Stillman |
| 4,107,452 A | 8/1978 | Razvi |
| 4,141,830 A | 2/1979 | Last |
| 4,179,616 A | 12/1979 | Coviello et al. |
| D254,266 S | 2/1980 | Tableriou |
| 4,214,971 A | 7/1980 | Heikel et al. |
| 4,230,571 A | 10/1980 | Dadd |
| 4,250,910 A | 2/1981 | King |
| 4,290,873 A | 9/1981 | Weaver |
| 4,435,095 A | 3/1984 | Jones et al. |
| 4,510,487 A | 4/1985 | Wolfe et al. |
| 4,535,247 A * | 8/1985 | Kurtz ................ A61L 2/24 250/436 |
| 4,752,401 A | 6/1988 | Bodenstein |
| 4,774,977 A | 10/1988 | Cohen |
| 4,781,810 A | 11/1988 | Tucker |
| 4,842,723 A | 6/1989 | Parks et al. |
| 4,849,115 A | 7/1989 | Cole et al. |
| 4,856,348 A | 8/1989 | Hall |
| 4,900,432 A | 2/1990 | Arnold et al. |
| 4,940,946 A | 7/1990 | Nazaryan |
| 4,959,142 A * | 9/1990 | Dempo ................ C02F 9/00 210/167.29 |
| 5,055,183 A | 10/1991 | Buchan |
| D326,309 S | 5/1992 | Kendrick |
| 5,115,222 A | 5/1992 | Peralta et al. |
| 5,124,032 A | 6/1992 | Newhard |
| 5,124,960 A | 6/1992 | Miller et al. |
| 5,152,610 A | 10/1992 | Hallett |
| 5,169,236 A | 12/1992 | Iest |
| 5,189,350 A | 2/1993 | Mallett |
| 5,217,261 A | 6/1993 | DeWitt et al. |
| 5,221,444 A | 6/1993 | Silveri |
| 5,228,964 A | 7/1993 | Middleby |
| 5,234,563 A | 8/1993 | Arai et al. |
| 5,247,710 A | 9/1993 | Carder et al. |
| 5,254,226 A | 10/1993 | Williams et al. |
| 5,266,215 A | 11/1993 | Engelhard |
| 5,279,748 A | 1/1994 | Hackett |
| 5,302,298 A | 4/1994 | Leitzke |
| 5,314,589 A | 5/1994 | Hawley |
| 5,326,481 A | 7/1994 | Alwerud |
| 5,362,368 A * | 11/1994 | Lynn ................ C02F 1/4674 204/234 |
| 5,401,373 A | 3/1995 | Silveri |
| 5,422,014 A | 6/1995 | Allen et al. |
| 5,422,487 A | 6/1995 | Sauska et al. |
| 5,434,419 A | 7/1995 | Decupper |
| 5,460,706 A | 10/1995 | Lisboa |
| 5,498,333 A | 3/1996 | Canther |
| 5,518,635 A | 5/1996 | Kohlman |
| D371,824 S | 7/1996 | Price et al. |
| 5,546,982 A | 8/1996 | Clark et al. |
| 5,580,438 A | 12/1996 | Silveri |
| 5,590,390 A | 12/1996 | Maarschalkerweerd |
| 5,649,560 A | 7/1997 | Lenney et al. |
| 5,681,110 A | 10/1997 | Burzacchi |
| 5,695,644 A | 12/1997 | Buchanan et al. |
| 5,709,799 A * | 1/1998 | Engelhard ................ C02F 1/325 210/748.1 |
| 5,730,861 A | 3/1998 | Sterghos et al. |
| 5,752,282 A | 5/1998 | Silveri |
| 5,759,384 A | 6/1998 | Silveri |
| 5,788,826 A | 8/1998 | Nyberg |
| 5,810,999 A | 9/1998 | Bachand et al. |
| 5,893,977 A | 4/1999 | Pucci |
| 5,915,622 A | 6/1999 | Foote |
| 5,925,572 A | 7/1999 | Byrne et al. |
| 5,932,093 A | 8/1999 | Chulick |
| 5,985,155 A | 11/1999 | Maitland |
| 5,993,669 A | 11/1999 | Fulmer |
| 5,996,138 A | 12/1999 | Kentch |
| 6,001,242 A | 12/1999 | England et al. |
| 6,007,693 A | 12/1999 | Silveri |
| 6,013,918 A | 1/2000 | Bushnell et al. |
| 6,027,642 A | 2/2000 | Prince et al. |
| D422,676 S | 4/2000 | Conover et al. |
| 6,071,473 A | 6/2000 | Darwin |
| 6,096,202 A | 8/2000 | Fulmer |
| 6,099,735 A | 8/2000 | Kelada |
| 6,099,799 A | 8/2000 | Anderson |
| 6,113,858 A | 9/2000 | Tang |
| 6,120,691 A | 9/2000 | Mancil |
| RE36,896 E | 10/2000 | Maarschalkerweerd |
| D432,206 S | 10/2000 | Stoltz et al. |
| 6,125,481 A | 10/2000 | Sicilano |
| 6,125,778 A | 10/2000 | Rodden |
| 6,126,810 A | 10/2000 | Fricker et al. |
| 6,129,850 A | 10/2000 | Martin et al. |
| 6,132,629 A | 10/2000 | Boley |
| 6,149,343 A | 11/2000 | Lewis et al. |
| 6,171,452 B1 | 1/2001 | Michael |
| RE37,055 E | 2/2001 | Silveri |
| 6,193,894 B1 | 2/2001 | Hollander |
| D439,313 S | 3/2001 | Wey et al. |
| 6,200,487 B1 | 3/2001 | Denkewicz, Jr. et al. |
| 6,210,566 B1 | 4/2001 | King |
| 6,217,754 B1 | 4/2001 | Ros |
| 6,221,257 B1 | 4/2001 | Grim |
| 6,223,359 B1 | 5/2001 | Oltmanns et al. |
| 6,225,900 B1 | 5/2001 | Keon et al. |
| 6,228,272 B1 | 5/2001 | Gola |
| 6,231,820 B1 | 5/2001 | Wedekamp |
| 6,235,188 B1 | 5/2001 | Nakamura et al. |
| 6,238,553 B1 | 5/2001 | Lin |
| 6,238,555 B1 | 5/2001 | Silveri et al. |

(56) References Cited

U.S. PATENT DOCUMENTS

| | | |
|---|---|---|
| 6,270,680 B1 | 8/2001 | Silveri et al. |
| 6,274,052 B1 | 8/2001 | Hartwig |
| 6,277,288 B1 * | 8/2001 | Gargas .................. C02F 1/4674 |
| | | 205/752 |
| 6,287,466 B1 | 9/2001 | Yassin |
| 6,294,086 B1 | 9/2001 | Reeves |
| 6,299,761 B1 | 10/2001 | Wang |
| 6,309,538 B1 | 10/2001 | Khan |
| 6,340,431 B2 | 1/2002 | Khan |
| 6,402,966 B1 | 6/2002 | Taira |
| 6,444,129 B1 | 9/2002 | Collins |
| 6,447,720 B1 | 9/2002 | Horton, III et al. |
| 6,447,721 B1 | 9/2002 | Horton, III et al. |
| 6,456,197 B1 | 9/2002 | Lauritsen et al. |
| 6,476,721 B1 | 11/2002 | Diebold |
| 6,488,841 B2 | 12/2002 | Glasgow |
| 6,541,771 B2 | 4/2003 | Iwabuchi et al. |
| 6,570,173 B1 | 5/2003 | Kunkel et al. |
| 6,579,446 B1 | 6/2003 | Teran et al. |
| D479,475 S | 9/2003 | Dermikaelien-Covault et al. |
| 6,620,315 B2 | 9/2003 | Martin |
| 6,620,318 B1 | 9/2003 | Neofotistos et al. |
| 6,623,647 B2 | 9/2003 | Martin |
| 6,625,824 B1 | 9/2003 | Lutz et al. |
| 6,653,842 B2 | 11/2003 | Mosley et al. |
| 6,685,825 B1 | 2/2004 | Chang |
| 6,697,706 B2 | 2/2004 | Gardner, Jr. |
| 6,713,298 B2 | 3/2004 | McDevitt et al. |
| 6,716,345 B2 | 4/2004 | Snyder |
| D489,431 S | 5/2004 | Antunez |
| 6,749,759 B2 | 6/2004 | Denes et al. |
| 6,756,907 B2 | 6/2004 | Rollaway |
| 6,761,827 B2 | 7/2004 | Coffey |
| 6,792,956 B2 | 9/2004 | Bredo et al. |
| 6,797,970 B1 | 9/2004 | Gatter et al. |
| 6,814,095 B2 | 11/2004 | King |
| 6,824,693 B1 | 11/2004 | Sauska et al. |
| 6,827,847 B1 | 12/2004 | Chauvier |
| 6,895,307 B2 | 5/2005 | Gardner, Jr. |
| 6,932,903 B2 | 8/2005 | Chang |
| 6,948,510 B2 | 9/2005 | King |
| 6,958,693 B2 | 10/2005 | Rothgeb et al. |
| 6,991,735 B2 | 1/2006 | Martin |
| 7,014,753 B2 | 3/2006 | Holstein et al. |
| 7,022,225 B1 | 4/2006 | Clawson et al. |
| 7,037,038 B1 | 5/2006 | Haski et al. |
| D526,382 S | 8/2006 | Thompson |
| D537,913 S | 3/2007 | Biberger et al. |
| 7,211,176 B2 | 5/2007 | Hin et al. |
| 7,292,898 B2 | 11/2007 | Clark et al. |
| D559,943 S | 1/2008 | Mercer |
| 7,329,343 B1 | 2/2008 | Barnes |
| 7,390,399 B2 | 6/2008 | Dennis, II et al. |
| 7,393,450 B2 | 7/2008 | Silveri |
| 7,402,252 B2 | 7/2008 | Kadlec et al. |
| 7,409,853 B2 | 8/2008 | Biberger et al. |
| 7,472,434 B1 | 1/2009 | Moldthan et al. |
| 7,507,323 B1 | 3/2009 | Eyal |
| 7,511,281 B2 | 3/2009 | Cooper |
| 7,612,492 B2 | 11/2009 | Lestician |
| 7,641,868 B2 | 1/2010 | Jang |
| 7,655,116 B1 * | 2/2010 | Tilsner .................... C23F 13/18 |
| | | 204/196.15 |
| 7,658,824 B2 | 2/2010 | Bremauer |
| 7,662,293 B2 | 2/2010 | Brolin et al. |
| 7,681,436 B2 | 3/2010 | Biberger |
| 7,687,785 B2 | 3/2010 | Chen |
| 7,691,343 B2 | 4/2010 | Ueberall |
| 7,695,613 B2 | 4/2010 | Doyle et al. |
| 7,722,746 B1 | 5/2010 | Eyal |
| 7,741,617 B2 | 6/2010 | Matthews et al. |
| 7,752,893 B2 | 7/2010 | Biberger |
| 7,754,090 B1 | 7/2010 | Berg |
| 7,767,067 B2 | 8/2010 | Silveri |
| 7,767,168 B2 | 8/2010 | Namespetra et al. |
| 7,794,608 B2 | 9/2010 | Denkewicz, Jr. et al. |
| 7,867,401 B2 | 1/2011 | Dennis, II et al. |
| 7,879,208 B2 | 2/2011 | Wu et al. |
| 7,901,620 B2 | 3/2011 | Taguchi et al. |
| 8,007,653 B2 * | 8/2011 | Porat .................... E04H 4/1281 |
| | | 15/1.7 |
| 8,043,500 B2 | 10/2011 | Murg |
| 8,048,316 B2 | 11/2011 | Denkewicz, Jr. |
| 8,066,940 B2 | 11/2011 | Denkewicz, Jr. et al. |
| 8,066,941 B2 | 11/2011 | Denkewicz, Jr. et al. |
| 8,075,751 B2 | 12/2011 | Xie et al. |
| 8,123,956 B2 | 2/2012 | King et al. |
| 8,241,586 B2 | 8/2012 | Burris et al. |
| 8,246,839 B2 | 8/2012 | Ueberall |
| 8,343,342 B2 | 1/2013 | Foret |
| 8,367,007 B2 | 2/2013 | Otero et al. |
| 8,414,839 B1 | 4/2013 | Barnes |
| 8,459,100 B2 | 6/2013 | Biberger |
| 8,475,725 B1 | 7/2013 | Antipenko et al. |
| 8,481,985 B2 | 7/2013 | Neister |
| 8,487,267 B2 | 7/2013 | Abe et al. |
| 8,491,775 B1 | 7/2013 | Barnes |
| 8,492,736 B2 | 7/2013 | Wang et al. |
| 8,496,610 B2 | 7/2013 | Levenson et al. |
| 8,506,886 B2 | 8/2013 | Owen et al. |
| 8,519,356 B2 | 8/2013 | Boyle |
| 8,529,770 B2 | 9/2013 | Yencho |
| 8,591,730 B2 | 11/2013 | Yong et al. |
| 8,883,079 B2 | 11/2014 | Clark |
| 8,887,556 B2 | 11/2014 | Silveri |
| 8,963,736 B2 | 2/2015 | Millar |
| 9,031,702 B2 * | 5/2015 | Pruchniewski .... G05B 19/0421 |
| | | 700/275 |
| 9,034,193 B2 | 5/2015 | Shalon |
| 9,097,234 B2 | 8/2015 | Breau et al. |
| 9,102,536 B2 | 8/2015 | Cannavino et al. |
| 9,581,478 B1 | 2/2017 | Smith |
| 9,631,388 B2 | 4/2017 | Hui et al. |
| D789,221 S | 6/2017 | Miller et al. |
| 9,815,719 B2 | 11/2017 | Sayre et al. |
| 9,834,451 B2 | 12/2017 | Miller et al. |
| 9,858,792 B2 | 1/2018 | Fernandes et al. |
| 9,885,193 B2 | 2/2018 | Chen et al. |
| 10,106,442 B2 | 10/2018 | Martin et al. |
| 10,127,362 B2 | 11/2018 | Bennett et al. |
| 10,156,081 B2 | 12/2018 | Chen et al. |
| 10,479,705 B2 | 11/2019 | Rochelle |
| 2001/0010296 A1 | 8/2001 | Hirota et al. |
| 2001/0045380 A1 | 11/2001 | Khan |
| 2002/0035403 A1 | 3/2002 | Clark et al. |
| 2002/0108913 A1 | 8/2002 | Collins |
| 2002/0125716 A1 | 9/2002 | Rochelle |
| 2002/0152036 A1 | 10/2002 | Martin |
| 2002/0195403 A1 | 12/2002 | Takeda et al. |
| 2003/0160005 A1 | 8/2003 | Martin |
| 2003/0168389 A1 | 9/2003 | Astle et al. |
| 2003/0227394 A1 | 12/2003 | Rothgeb et al. |
| 2004/0031329 A1 | 2/2004 | Carpenter et al. |
| 2004/0050781 A1 | 3/2004 | Coffey et al. |
| 2004/0066313 A1 | 4/2004 | Ong et al. |
| 2004/0197229 A1 | 10/2004 | Runyon |
| 2004/0204779 A1 | 10/2004 | Mueller et al. |
| 2004/0206706 A1 | 10/2004 | Costa et al. |
| 2004/0208499 A1 | 10/2004 | Grober |
| 2004/0249579 A1 | 12/2004 | Centanni |
| 2005/0009192 A1 | 1/2005 | Page |
| 2005/0051741 A1 | 3/2005 | Hallett et al. |
| 2005/0109793 A1 | 5/2005 | Thomas |
| 2005/0137118 A1 | 6/2005 | Silveri |
| 2005/0162273 A1 | 7/2005 | Yoon et al. |
| 2005/0207939 A1 | 9/2005 | Roussi et al. |
| 2005/0220169 A1 | 10/2005 | McGowan-Scanlon |
| 2005/0222786 A1 | 10/2005 | Tarpo et al. |
| 2005/0225766 A1 | 10/2005 | Hansen et al. |
| 2005/0279677 A1 | 12/2005 | Lin |
| 2006/0027463 A1 | 2/2006 | Lavelle et al. |
| 2006/0054567 A1 * | 3/2006 | Mousseau ............... C02F 1/467 |
| | | 210/748.17 |
| 2006/0060512 A1 | 3/2006 | Astle et al. |

(56) References Cited

U.S. PATENT DOCUMENTS

| | | |
|---|---|---|
| 2006/0091002 A1 | 5/2006 | Hin et al. |
| 2006/0096927 A1 | 5/2006 | Clukies |
| 2006/0097878 A1 | 5/2006 | Von Broembsen |
| 2006/0113256 A1 | 6/2006 | Birkbeck |
| 2006/0144689 A1 | 7/2006 | Barnes et al. |
| 2006/0144691 A1 | 7/2006 | Barnes et al. |
| 2006/0169647 A1 | 8/2006 | Doyle et al. |
| 2006/0196525 A1 | 9/2006 | Vrtis et al. |
| 2006/0249400 A1 | 11/2006 | Bremauer |
| 2006/0266682 A1 | 11/2006 | Kennedy et al. |
| 2006/0283789 A1 | 12/2006 | Kadlec et al. |
| 2006/0283808 A1 | 12/2006 | Kadlec et al. |
| 2007/0013381 A1 | 1/2007 | Biberger |
| 2007/0061051 A1 | 3/2007 | Maddox |
| 2007/0144911 A1 | 6/2007 | Pulis |
| 2007/0154322 A1 | 7/2007 | Stiles et al. |
| 2007/0158274 A1 | 7/2007 | King |
| 2007/0181439 A1 | 8/2007 | Wu et al. |
| 2007/0181498 A1 | 8/2007 | Kaas |
| 2007/0215531 A1 | 9/2007 | Wawrla et al. |
| 2007/0244576 A1 | 10/2007 | Potucek et al. |
| 2007/0248488 A1 | 10/2007 | Denkewicz |
| 2008/0039977 A1 | 2/2008 | Clark et al. |
| 2008/0142452 A1 | 6/2008 | Denkewicz et al. |
| 2008/0173574 A1 | 7/2008 | Silveri |
| 2008/0212782 A1 | 9/2008 | Brettle et al. |
| 2008/0237148 A1 | 10/2008 | Dennis et al. |
| 2008/0264447 A1 | 10/2008 | Eyal |
| 2008/0289706 A1 | 11/2008 | King et al. |
| 2008/0311898 A1 | 12/2008 | Benco et al. |
| 2009/0060269 A1 | 3/2009 | Rhoads |
| 2009/0185953 A1 | 7/2009 | Hallam et al. |
| 2009/0208386 A1 | 8/2009 | Barsky et al. |
| 2009/0212782 A1 | 8/2009 | Silveri |
| 2009/0218296 A1 | 9/2009 | King et al. |
| 2009/0243852 A1 | 10/2009 | Haupt et al. |
| 2009/0266231 A1 | 10/2009 | Franzen et al. |
| 2009/0269240 A1 | 10/2009 | Tanaka |
| 2009/0282627 A1 | 11/2009 | Porat |
| 2009/0294381 A1 | 12/2009 | Coffey et al. |
| 2009/0303055 A1 | 12/2009 | Anderson et al. |
| 2010/0015013 A1 | 1/2010 | Sutton |
| 2010/0018930 A1 | 1/2010 | King et al. |
| 2010/0025337 A1 | 2/2010 | Yencho |
| 2010/0032355 A1 | 2/2010 | Andrews et al. |
| 2010/0059455 A1 | 3/2010 | Hsueh et al. |
| 2010/0096260 A1 | 4/2010 | Xie et al. |
| 2010/0096338 A1 | 4/2010 | De Wet et al. |
| 2010/0101010 A1 | 4/2010 | McCague |
| 2010/0187122 A1 | 7/2010 | Zolotarsky et al. |
| 2010/0206815 A1 | 8/2010 | Garusi et al. |
| 2010/0209294 A1 | 8/2010 | Owen et al. |
| 2010/0237254 A1 | 9/2010 | Mason et al. |
| 2010/0250449 A1 | 9/2010 | Doyle et al. |
| 2010/0254825 A1 | 10/2010 | Stiles, Jr. et al. |
| 2010/0258508 A1 | 10/2010 | Levy |
| 2010/0313524 A1 | 12/2010 | Pape et al. |
| 2010/0313964 A1 | 12/2010 | Hin et al. |
| 2011/0009019 A1 | 1/2011 | Neira et al. |
| 2011/0010835 A1 | 1/2011 | McCague |
| 2011/0048964 A1 | 3/2011 | Luebke et al. |
| 2011/0049060 A1 | 3/2011 | Uy |
| 2011/0062086 A1 | 3/2011 | Burns et al. |
| 2011/0073488 A1 | 3/2011 | Hsiang Lin |
| 2011/0214500 A1 | 9/2011 | Cabrera et al. |
| 2011/0278158 A1 | 11/2011 | Briggs et al. |
| 2011/0290707 A1 | 12/2011 | Porat |
| 2011/0318237 A1 | 12/2011 | Woodling et al. |
| 2012/0051977 A1 | 3/2012 | Boodaghians et al. |
| 2012/0327657 A1 | 12/2012 | Pickard et al. |
| 2013/0048545 A1 | 2/2013 | Shatalov et al. |
| 2013/0104321 A1 | 5/2013 | Michelon |
| 2013/0105372 A1 | 5/2013 | Chen et al. |
| 2013/0105373 A1 | 5/2013 | Chen et al. |
| 2013/0105403 A1 | 5/2013 | Chen et al. |
| 2013/0146783 A1 | 6/2013 | Boodaghians et al. |
| 2013/0313204 A1 | 11/2013 | Shalon |
| 2014/0200840 A1 | 7/2014 | Cox et al. |
| 2014/0202948 A1 | 7/2014 | Li |
| 2014/0216926 A1* | 8/2014 | Shirato .............. C02F 1/46104 204/232 |
| 2014/0263091 A1 | 9/2014 | Carter, III et al. |
| 2014/0326680 A1 | 11/2014 | Mastio |
| 2014/0336821 A1* | 11/2014 | Blaine ................. A61H 33/005 700/275 |
| 2015/0268136 A1* | 9/2015 | Detweiller .............. G01N 1/14 73/864.34 |
| 2015/0308091 A1* | 10/2015 | Foust ..................... E03D 13/00 4/309 |
| 2015/0310634 A1 | 10/2015 | Babcock et al. |
| 2016/0042629 A1 | 2/2016 | Snyder |
| 2016/0108531 A1 | 4/2016 | Shanahan et al. |
| 2016/0122208 A1 | 5/2016 | Denkewicz et al. |
| 2016/0122210 A1 | 5/2016 | Cosac Albu |
| 2016/0131608 A1 | 5/2016 | Howes, Jr. |
| 2016/0178594 A1* | 6/2016 | Jarvis ................. G01N 33/1886 436/52 |
| 2016/0186357 A1 | 6/2016 | Stewart et al. |
| 2016/0259348 A1 | 9/2016 | Lewis et al. |
| 2016/0266577 A1 | 9/2016 | Kerzner |
| 2017/0066667 A1 | 3/2017 | Harris |
| 2017/0203980 A1 | 7/2017 | Buzaglo et al. |
| 2017/0283279 A1 | 10/2017 | Pelletier et al. |
| 2017/0336381 A1 | 11/2017 | Zeevi |
| 2018/0118581 A1 | 5/2018 | Miller et al. |
| 2018/0130328 A1 | 5/2018 | Fernandes et al. |
| 2018/0160694 A9 | 6/2018 | Foret |
| 2018/0163420 A1 | 6/2018 | Chen et al. |
| 2018/0354833 A1 | 12/2018 | Van Riper et al. |
| 2019/0087548 A1 | 3/2019 | Bennett et al. |
| 2019/0119937 A1 | 4/2019 | Chen et al. |
| 2019/0127253 A1 | 5/2019 | Thomas et al. |

FOREIGN PATENT DOCUMENTS

| | | |
|---|---|---|
| CN | 103245766 A | 8/2013 |
| CN | 104251730 A | 12/2014 |
| CN | 204165969 U | 2/2015 |
| CN | 204495401 U | 7/2015 |
| DE | 3441535 A1 | 6/1986 |
| DE | 19951436 A1 | 5/2000 |
| DE | 19921436 A1 | 11/2000 |
| DE | 102006013628 A1 | 9/2007 |
| EP | 0821514 A1 | 1/1998 |
| EP | 1600749 A1 | 11/2005 |
| EP | 1602628 A1 | 12/2005 |
| EP | 1913216 A2 | 4/2008 |
| EP | 2567713 A1 | 3/2013 |
| GB | 2365122 A | 2/2002 |
| JP | H11-87770 A | 3/1999 |
| WO | 03/012434 A2 | 2/2003 |
| WO | 03/087501 A1 | 10/2003 |
| WO | 03/091668 A2 | 11/2003 |
| WO | 2004/019295 A1 | 3/2004 |
| WO | 2004/071965 A1 | 8/2004 |
| WO | 2005/008443 A2 | 1/2005 |
| WO | 2005/105675 A1 | 11/2005 |
| WO | 2009/006702 A1 | 1/2009 |
| WO | 2009/013507 A1 | 1/2009 |
| WO | 2009/052831 A1 | 4/2009 |
| WO | 2011/009170 A1 | 1/2011 |
| WO | 2014/115146 A1 | 7/2014 |

OTHER PUBLICATIONS

Written Opinion of the International Searching Authority dated Jul. 5, 2018, issued in connection with International Application No. PCT/US18/23514 (6 pages).

Invitation to Pay Additional Fees and, Where Applicable, Protest Fee dated May 8, 2018, issued in connection with International Patent Application No. PCT/US18/23514 (2 pages).

(56) References Cited

OTHER PUBLICATIONS

Clearwater In-Line Chlorinator Installation Instructions, Waterway Plastics, 2008 (2 pages).
"Jandy Installation and Operation Manual" Zodiac Pool Systems, Inc. 2010 (15 pages).
"Jandy UltraFlex 2 Installation and Maintenance Guide," Zodiac Pool Systems, Inc., 2009 (23 pages).
Hayward "Salt and Swim Installation Quick Start Guide," earliest known date May 28, 2012 (from waybackmachine.com) (2 pages).
Partial Supplementary European Search Report dated Oct. 26, 2015, issued by the European Patent Office in connection with European Patent Application No. 12820228.0 (6 pages).
Extended European Search Report dated Feb. 17, 2016, issued by the European Patent Office in connection with European Patent Application No. 12820228.0 (13 pages).
Extended European Search Report dated Jul. 1, 2015, issued by the European Patent Office in connection with European Patent Application No. 12820744.6 (7 pages).
Extended European Search Report dated May 7, 2015, issued by the European Patent Office in connection with European Patent Application No. 12820373.4 (5 pages).
Communication Pursuant to Article 94(3) dated Oct. 4, 2017, issued by the European Patent Office in connection with European Patent Application No. 12820373.4 (4 pages).
International Search Report of the International Searching Authority dated Sep. 28, 2012, issued in connection with International Patent Application No. PCT/US12/48888 (4 pages).
Written Opinion of the International Searching Authority dated Sep. 28, 2012, issued in connection with International Patent Application No. PCT/US12/48888 (6 pages).
International Search Report of the International Searching Authority dated Oct. 1, 2012, issued in connection with International Patent Application No. PCT/US12/48874 (4 pages).
Written Opinion of the International Searching Authority dated Oct. 1, 2012, issued in connection with International Patent Application No. PCT/US12/48874 (5 pages).
International Search Report of the International Searching Authority dated Dec. 19, 2012, issued in connection with International Patent Application No. PCT/US12/48891 (5 pages).
Written Opinion of the International Searching Authority dated Dec. 19, 2012, issued in connection with International Patent Application No. PCT/US12/48891 (6 pages).
International Search Report of the International Searching Authority dated May 9, 2014, issued in connection with International Application No. PCT/US14/13390 (3 pages).
Written Opinion of the International Searching Authority dated May 9, 2014, issued in connection with International Patent Application No. PCT/US2014/013390 (8 pages).
Office Action dated Apr. 28, 2015, issued in connection with U.S. Appl. No. 13/562,128 (18 pages).
Office Action dated Jan. 21, 2016, issued in connection with U.S. Appl. No. 13/562,128 (19 pages).
Office Action dated Jan. 5, 2017, issued in connection with U.S. Appl. No. 13/562,128 (19 pages).
Notice of Allowance dated Jun. 28, 2017 issued in connection with U.S. Appl. No. 13/562,128 (8 pages).
Notice of Allowance dated Sep. 14, 2017 issued in connection with U.S. Appl. No. 13/562,128 (8 pages).
Notice of Allowance dated Nov. 7, 2017 issued in connection with U.S. Appl. No. 13/562,128 (9 pages).
Office Action dated Aug. 24, 2015, issued in connection with U.S. Appl. No. 13/561,836 (12 pages).
Office Action dated May 25, 2016, issued in connection with U.S. Appl. No. 13/561,836 (14 pages).
Office Action dated Sep. 12, 2016, issued in connection with U.S. Appl. No. 13/561,836 (22 pages).
Office Action dated Nov. 20, 2017, issued in connection with U.S. Appl. No. 13/561,836 (29 pages).
Office Action dated Mar. 31, 2015, issued in connection with U.S. Appl. No. 13/562,043 (13 pages).
Office Action dated Oct. 2, 2015, issued in connection with U.S. Appl. No. 13/562,043 (11 pages).
Office Action dated Jun. 22, 2016, issued in connection with U.S. Appl. No. 13/562,043 (16 pages).
Office Action dated Feb. 14, 2017, issued in connection with U.S. Appl. No. 13/562,043 (19 pages).
Office Action dated Oct. 4, 2017, issued in connection with U.S. Appl. No. 13/562,043 (26 pages).
Office Action dated May 7, 2018, issued in connection with U.S. Appl. No. 13/562,043 (31 pages).
Patent Examination Report No. 1, dated Jul. 29, 2016, issued in connection with Australian Application No. 2012290292 (3 pages).
Patent Examination Report No. 2, dated Jun. 22, 2017, issued in connection with Australian Application No. 2012290292 (5 pages).
Patent Examination Report No. 1, dated May 13, 2016, issued in connection with Australian Application No. 2012290215 (4 pages).
Patent Examination Report No. 1, dated Nov. 17, 2017, issued in connection with Australian Application No. 2017203145 (4 pages).
Patent Examination Report No. 1, dated Sep. 16, 2016, issued in connection with Australian Application No. 2012290213 (5 pages).
Patent Examination Report No. 2, dated Sep. 4, 2017, issued in connection with Australian Application No. 2012290213 (5 pages).
Patent Examination Report No. 3, dated Sep. 14, 2017, issued in connection with Australian Application No. 2012290213 (5 pages).
International Preliminary Report on Patentability dated Feb. 13, 2014 issued in connection with International Application No. PCT/US12/48874 (7 pages).
International Preliminary Report on Patentability dated Aug. 2, 2016 issued in connection with International Application No. PCT/US14/13390 (9 pages).
Notice of Allowance dated Aug. 24, 2018, issued in connection with U.S. Appl. No. 13/561,836 (13 pages).
Communication pursuant to Article 94(3) EPC dated Sep. 21, 2018, issued by the European Patent Office in connection with European Patent Application No. 12820744.6 (8 pages).
Interview Summary dated Nov. 8, 2019, issued in connection with U.S. Appl. No. 15/889,849 (2 pages).
Examination Report No. 2, dated Nov. 11, 2019, issued in connection with Australian Application No. 2017228646 (4 pages).
Office Action dated Dec. 2, 2019, issued in connection with U.S. Appl. No. 15/889,849 (15 pages).
Office Action dated Jan. 22, 2020, issued in connection with U.S. Appl. No. 16/223,500 (21 pages).
D. W. Egles, "RANGER 1: A Self-Propelled Data Buoy," OCEANS '85—Ocean Engineering and the Environment, IEEE Conference Record, Nov. 1985, vol. 1, pp. 56-61.
William R. Griffen, "Maintaining Swimming Pools, Spas, Whirlpool Tubs, and Saunas" (2001), retrieved from the internet at <http://www.cleaningconsultants.com/pages/articles/poolsspas.html> (8 pages).
"Water Chemistry for Swimming Pools", North Carolina Department of Environment and Natural Resources, Feb. 2001, retreived from the internet archive at <https://web.archive.org/web/20010207022454/http://www.deh.enr.state.nc.us/ehs/quality/wph.htm> (12 pages).
Denkewicz, et al., "Co-Generation of UV, Ozone, and Hydroxyl Radicals and its Strategic Use for Aquatic Treatment," PowerPoint presentation presented at World Aquatic Health Conference in Indianapolis, IN, Oct. 18, 2013 (61 pages).
Denkewicz, "UV & Ozone Working Together to Improve Water Quality," Water Quality Products, May 2008 (2 pages).
Denkewicz, "The Efficacy of a Combined Approach," Water Quality Products, Water Disinfection, vol. 12, No. 2, Feb. 2007 (3 pages).
INYO Pools Forum, "UV/Ozone/Salt" discussion thread, Dec. 14, 2016, https://www.inyopools.com/Forum/thread/uv-ozone-salt/ (3 pages).
"Resilience D Chlorine Generator for small to large size swimming pools," Magen Eco-Energy webpage, believed to be publically accessible prior to Mar. 21, 2017, https://www.magen-ecoenergy.com/resilience_d/ (3 pages).
Examination Report No. 1, dated Dec. 21, 2018, issued in connection with Australian Application No. 2017228646 (4 pages).

(56) References Cited

OTHER PUBLICATIONS

Office Action dated Feb. 28, 2019, issued in connection with U.S. Appl. No. 16/223,500 (16 pages).
Office Action dated May 7, 2019, issued in connection with U.S. Appl. No. 15/889,849 (14 pages).
Examination Report dated Jun. 17, 2019, issued by the European Patent Office in connection with European Patent Application No. 12820228.0 (8 pages).
Office Action dated Jul. 9, 2019, issued in connection with U.S. Appl. No. 16/223,500 (14 pages).
Examination Report dated Jul. 11, 2019, issued by the European Patent Office in connection with European Patent Application No. 12820373.4 (4 pages).
AstralPool, Neolysis Installation and Maintenance Manual, version dated Aug. 8, 2016 (40 pages).
"Disinfection Equipment" AstralPool archived webpage dated Mar. 21, 2017 <http://web.archive.org/web/20170321051150/http:/www.astralpool.com:80/en/products/swiimming-pool/disinfection-equipment-11> (2 pages).
"Neolysis Equipment" AstralPool archived webpage dated Apr. 28, 2017 <http://web.archive.org/web/20170428222051/http:/www.astralpool.com/en/products/swiimming-pool/disinfection-equipment-1/neolysis-aquipment-4/> (1 page).
"Neolysis LS (1.5-3 g/I) + UV for Private Pools" AstralPool archived webpage dated Jul. 9, 2017 <http://web.archive.org/web/20170709212113/http:/www.astralpool.com/en/products/swiimming-pool/disinfection-equipment-1/neolysis-equipment-4/private-pools-neolysis-1/> (2 pages).
Atmel Corporation, "Crypto Products Customer Guide" dated Jun. 30 2009, retrieved from website <https://www.mouser.com/catalog/supplier/library/pdf/atmel_crypto-psguide_pdf> on Mar. 24, 2020 (26 pages).
Summons to Attend Oral Proceedings dated Apr. 29, 2020, in connection with European Patent Application No. 12820228.0 (9 pages).
Examination Report dated May 18, 2020, issued by the European Patent Office in connection with European Patent Application No. 12820744.6 (5 pages).
Office Action dated Jun. 8, 2020, issued in connection with U.S. Appl. No. 15/889,849 (16 pages).
Partial Supplementary European Search Report dated Jul. 17, 2020, issued by the European Patent Office in connnection with European Patent Application No. 18772389.5 (11 pages).
Notice of Allowance dated Oct. 20, 2020, issued in connection with U.S. Appl. No. 15/889,849 (7 pages).
Extended European Search Report dated Oct. 16, 2020, issued by the European Patent Office in connection with European Patent Application No. 18772389.5 (10 pages).
Decision to Refuse dated Dec. 22, 2020, in connection with European Patent Application No. 12820228.0 (10 pages).
CMP Powerclean Salt Ultra Installation Instructions and Product Manual (Nov. 2018), retrieved from www.c-m-p.com/pool-products/pool-sanitizers/powerclean-salt-systems/manuals-literature (24 pages).

* cited by examiner

SYSTEMS AND METHODS FOR SANITIZING POOL AND SPA WATER

RELATED APPLICATIONS

The present application claims priority to U.S. Provisional Application Ser. No. 62/474,333 filed on Mar. 21, 2017, the entire disclosure of which is expressly incorporated by reference herein in its entirety

BACKGROUND

Field of the Disclosure

The present disclosure relates generally to the field of pool and spa equipment. More particularly, the present disclosure relates to systems and methods for sanitizing pool and spa water.

RELATED ART

Fluid sanitization systems have been provided in the past for sanitizing pool and spa water. For example, assemblies for sanitizing and/or disinfecting water have been developed. Fluid (e.g., water) sanitization assemblies are useful in a myriad of different environments for various uses/applications, such as commercial and/or industrial applications. While such systems have various features and advantages, there is a constant need to improve the effectiveness of such systems. Accordingly, this and other needs are addressed by the systems and methods for sanitizing pool and spa water, of the present disclosure.

SUMMARY

Provided herein are systems and methods for sanitizing pool and spa water. In one embodiment, an electrolytic chlorinator (sometimes referred to herein as a salt cell) is provided which includes a combined flow, temperature, and salt concentration sensor. In another embodiment, the electrolytic chlorinator includes an acid tank for in-situ cleaning of the electrolytic chlorinator or acidification of pool/spa water where needed. In another embodiment, a delayed polarity reversal technique is provided for de-scaling and managing passivation of the blades of an electrolytic chlorinator. In still another embodiment, the electrolytic chlorinator includes a sacrificial anode for protecting components of the chlorinator as well as other pool/spa components. In yet another embodiment, the electrolytic chlorinator includes an integral, electrically-controlled acid generator. In another embodiment, the electrolytic chlorinator includes a brine tank for periodically superchlorinating and/or shocking pool/spa water. In still another embodiment, the chlorinator includes a plurality of chemical tanks/feeds for periodically injecting chemicals into the chlorinator. In another embodiment, a combined ultraviolet (UV)/Ozone and salt (electrolytic) chlorine generator is provided. In other embodiments, filters having integral UV sanitizers are provided. In still further embodiments, reflective linings are provided for UV sanitization systems. In another embodiment, a UV/Ozone sanitizer having means for injecting bubbles into pool/spa water is provided. In another embodiment, a system for acquiring and analyzing samples of pool/spa water using an unmanned aircraft (drone) is provided. Potential applications for the technologies disclosed herein include, but are not limited to, pools, spas, hot tubs, cooling towers, mister systems, secondary and tertiary waste water, rainwater, drinking water, industrial water treatment, aquaculture, and agriculture.

BRIEF DESCRIPTION OF THE DRAWINGS

The foregoing features of the disclosure will be apparent from the following Detailed Description, taken in connection with the accompanying drawings, in which.

DETAILED DESCRIPTION

The present disclosure relates to systems and methods for sanitizing pool/spa water, as described in detail below in connection with FIGS. 1-16.

Figure 1:
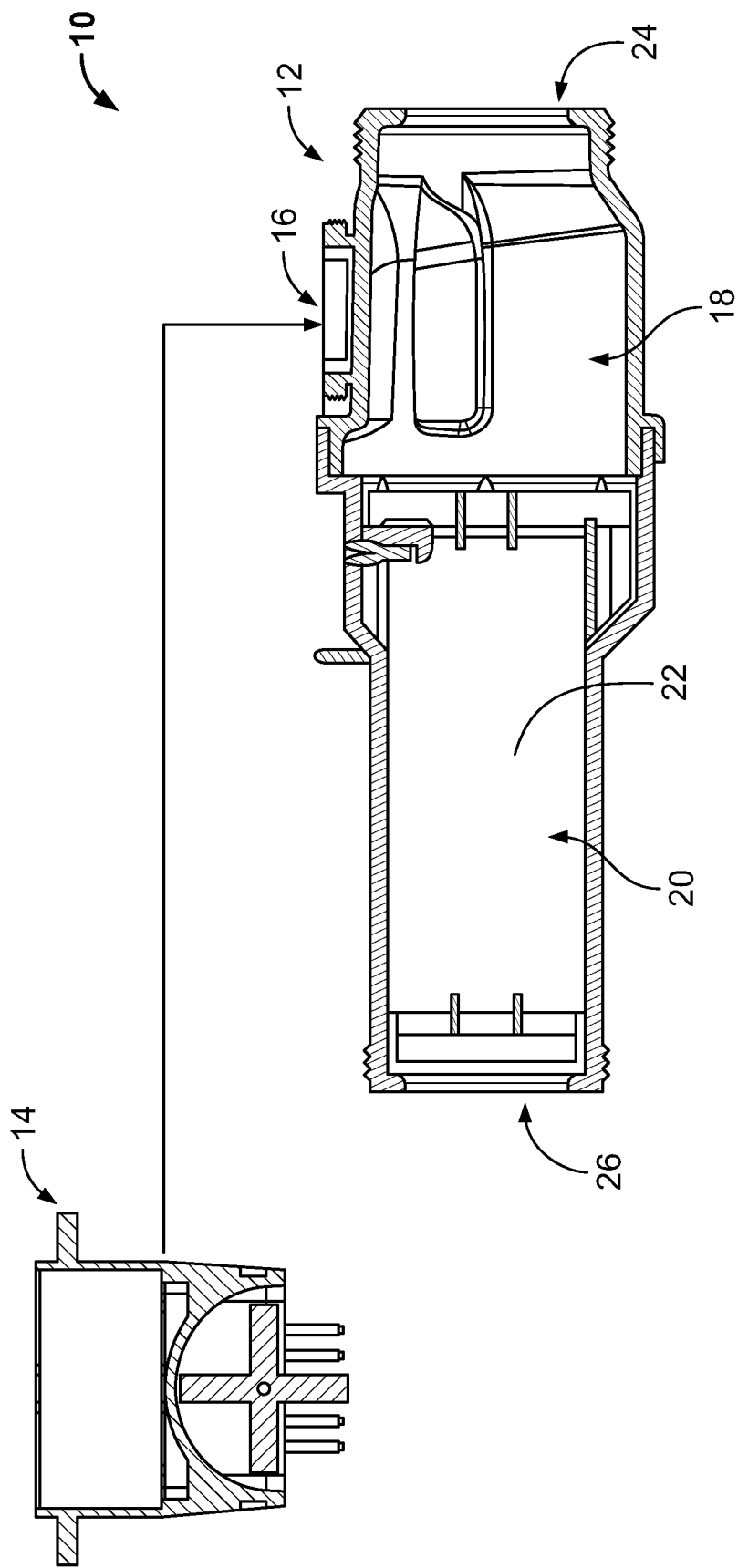
FIG. 1 is a diagram illustrating an electrolytic chlorinator having an combined flow and salt concentration sensor.

FIG. 1 is a diagram illustrating an electrolytic chlorinator 10 in accordance with the present invention. The chlorinator 10 can operate with a pumping system of a pool and/or spa, and sanitizes water of the pool and/or spa by converting salt within the water to free chlorine via electrolysis. The chlorinator 10 includes a body 12, a combined flow, temperature, and salt sensor 14 that is removably installed in an aperture 16 in the body and extends into a chamber 18 of the body, a forward portion 20 which includes a plurality of electrolytic plates 22, and ports 24, 26. It is noted that the combined flow and salt sensor 14 is installed in the aperture 16 in the general direction shown by the arrow in FIG. 1.

Figure 2:
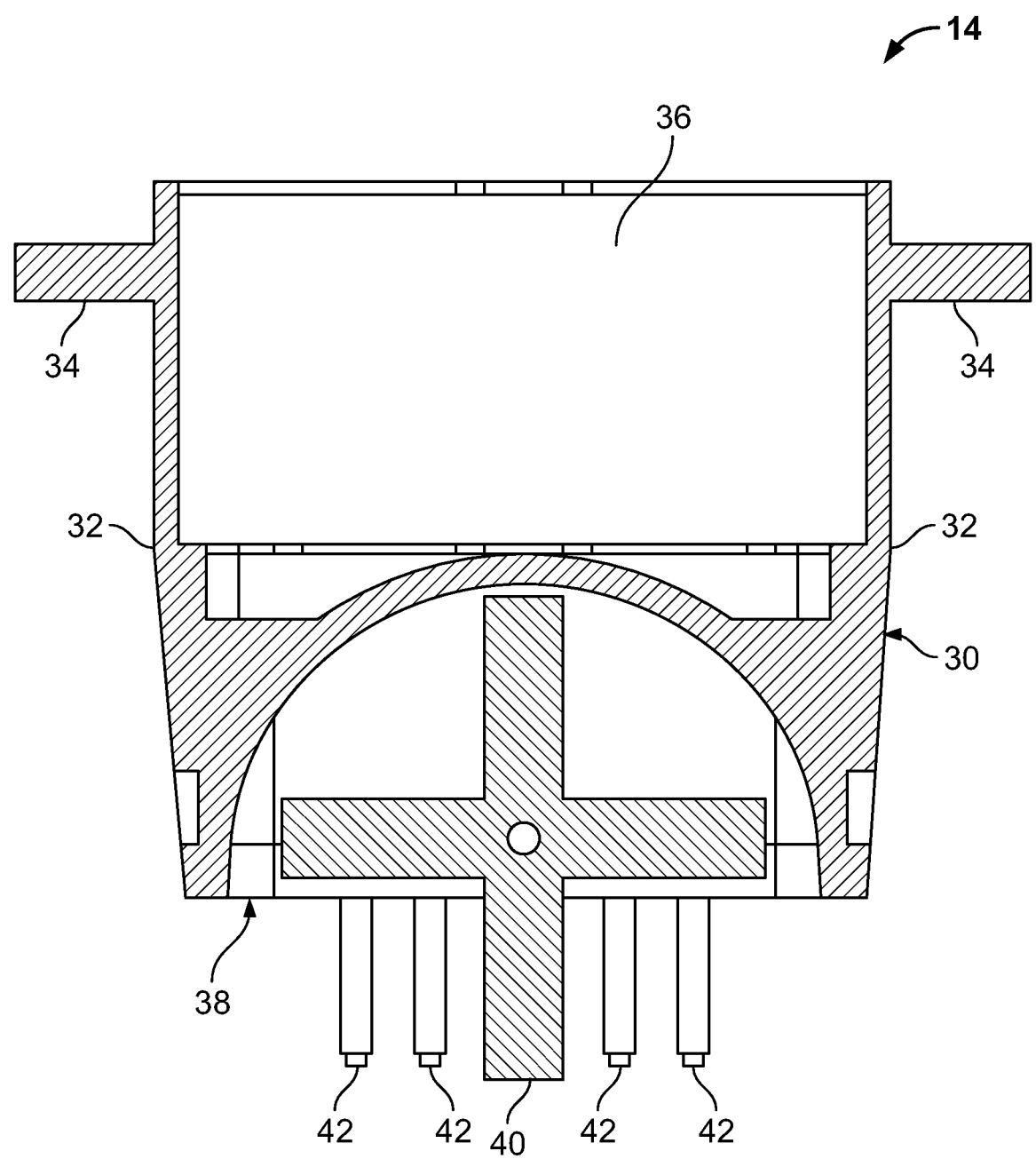
FIG. 2 is a diagram illustrating the combined flow and salt concentration sensor of FIG. 1 in greater detail.

FIG. 2 is a diagram illustrating the combined flow, temperature, and salt sensor 14 in greater detail. The sensor 14 includes a body 30 having a generally cylindrical outer wall 32 and a peripheral shoulder 34, a chamber 36 that receives a circuit board and/or electronics, potting compound 36 which encapsulates the circuit board and/or electronics, a recessed portion 38, a paddle wheel 40 which is at least partially positioned in the recessed portion 38, and a plurality of electrodes (pins) 42. As can be seen, 4 pins 42 are provided, but other quantities of pins could be provided without departing from the spirit or scope of the present disclosure. The paddle wheel 40 is in mechanical communication with a flow meter forming part of the sensor 14, and rotates whenever water flows past the sensor 14 to measure the rate of water flow past the sensor 14.

The sensor 14 measures the salt concentration in pool/spa water, as well as water's conductivity. Unlike 2-pin sensors, there is no interference from 'fouling' (e.g. scaling) and no calibration is required for the sensor 14. The sensor 14 can be located inside a salt cell (electrolytic chlorinator or other piece of pool equipment—e.g. pump, heater, etc.). Locating the sensor 14 inside a salt cell (or other pool equipment) eliminates the need for the sensor to be plumbed somewhere else in the system. Also, it allows the salt cell to intelligently know to shut itself off—it can do this because a change of conductivity occurs when water stops flowing and the gasses generated by the salt cell start to void the cell of liquid. When the sensor 14 stops being surrounded by water, the conductivity changes dramatically and can be detected and used for salt cell control (to control the chlorinator 10).

The sensor 14 can be used for cell health monitoring and diagnostics. The measured salt level from the sensor 14 can be compared with a calculated salt level based on an algorithm involving cell voltage, cell amperage and water temperature. In the comparison between 'measured' and 'calculated' salt, it is possible to discern how the salt cell is performing versus how it should be performing—the difference can intelligently inform if the cell is dirty (and needs to be cleaned) or if the cell is permanently degraded (and how much lifetime remains). Another advantage of the sensor 14 is that it can be used, in combination with the volume of pool or spa water, to inform the user of the actual pounds (or kilograms) of salt that needs to be added to the pool/spa in order to raise the salt concentration to a target level. Further, the salt concentration measured by the sensor can be compared to an impedance of plates of an electrolytic chlorinator in which the sensor is installed to determine a difference, and a condition of the electrolytic chlorinator can be determined based on the difference (which can be monitored over time).

The flow sensor of the sensor 14 can measure the presence of flowing water and the actual water flow rate. Installation of flow sensor in a salt cell or other piece of pool equipment (e.g. pump, heater) eliminates the need for a separate flow switch to be plumbed somewhere else in the system. The rotation of the paddle wheel 40 can be bidirectional, permitting flow detection and measurement in either flow direction. Magnets on the end of each rotary vane of the paddle wheel 40 can be detected by electronics in potted housing 36. The force required to rotate the paddle wheel 40 is very small, permitting detection of very low flow rates (e.g. <10 GPM). The paddle wheel 40 is scalable and can be used in small pipe and large pipe diameters (e.g. ½ inch pipe to 8 inch pipe and beyond). Further, paddle wheel 40 eliminates failure modes that falsely report flow. Calculation of pool turnover (i.e. how many gallons of water was processed in a 24 hour period divided by the volume of the pool) is also possible using flow measurements. Calibration of pump RPM and pump energy consumption to the flow rate for a given pool pad arrangement can also be performed, allowing for the calculation of electrical energy used to operate pool daily/weekly, annually, etc.

Additionally, calculation of optimal mixing and turnover rates for improved chemical sensing and dosing algorithms (e.g. prevent over oscillation) can be performed. A display could be provided for displaying flow rate and historical flow rates in a chlorinator (or a pump or a heater). Further, sensor 14 eliminates filter schedules by filtering as long as needed to meet specific water turnover goals and at the best energy level (e.g. run as slow and as long as you allow the pool to run). The sensor 14 enables a combination of flow rate (and flow history) with pump power sensing to predict whether there is a system leak. If pool plumbing has a significant leak then pump energy could decrease dramatically at constant flow rate or pump energy could remain constant yet there be a dramatic increase in flow rate. Additionally, the sensor 14 enables a combination of flow sensing and pump relay in order to 1) build a hydraulic curve for the plumbing, 2) determine practical maximum flow rate, 3) determine turnover schedule requirements, and 4) sense the filter media health. Still further, the sensor 14 enables a combination of flow sensing and certain controlled equipment in order to dynamically set the correct flow to meet 1) heater requirements when heating, 2) chlorinator needs when chlorinating, 3) adequate mixing of dosed chemicals such as acid or liquid chlorine when dosing.

Figure 3:
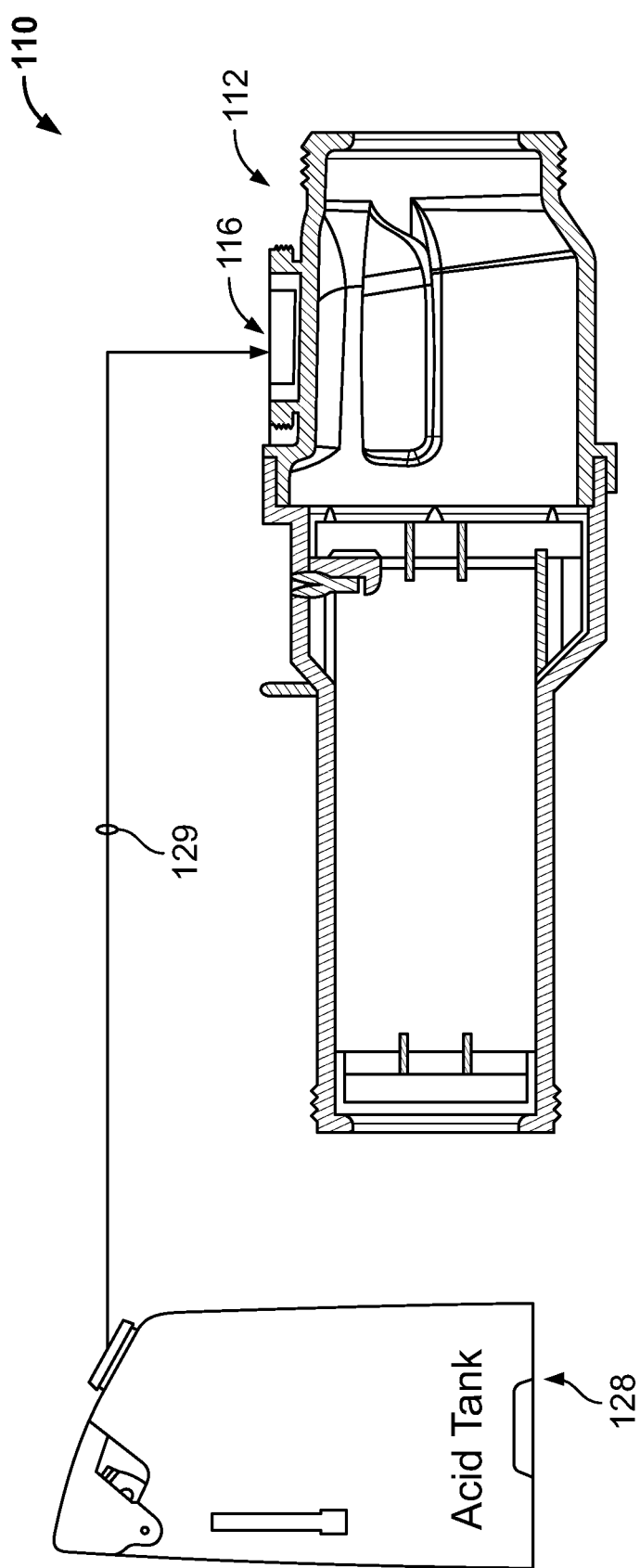
FIG. 3 is a diagram illustrating an electrolytic chlorinator having an acid tank for in-situ cleaning of the chlorinator and/or acid introduction into pool/spa water.

FIG. 3 is a diagram illustrating another embodiment of the sanitization system of the present disclosure, wherein an electrolytic chlorinator (salt cell) 110 with periodic in-situ acid cleaning capability is provided. In this embodiment, the chlorinator 110 is fed acid from an acid tank 128 via tubing 129 in fluid communication with a port 116 in the housing 112 of the chlorinator. A 'cell cleaning cycle' could be provided which automatically injects some (or all of the acid) that is expected to be needed (in a given week, for example) by the pool based on the salt chlorinator runtime and pool size directly into the salt cell to permit cleaning of scale from the salt cell. The system could inject a small amount of acid directly into cell 110 just prior to a pump turning on (e.g. 1 hour before), so as to take advantage of the high acid level on the electrodes yet rinsing it clean after this short exposure time. Alternatively, the system could inject a small amount of acid directly into cell after the pump has turned off to allow acid to soak inside cell and remove scale.

Figure 4A:
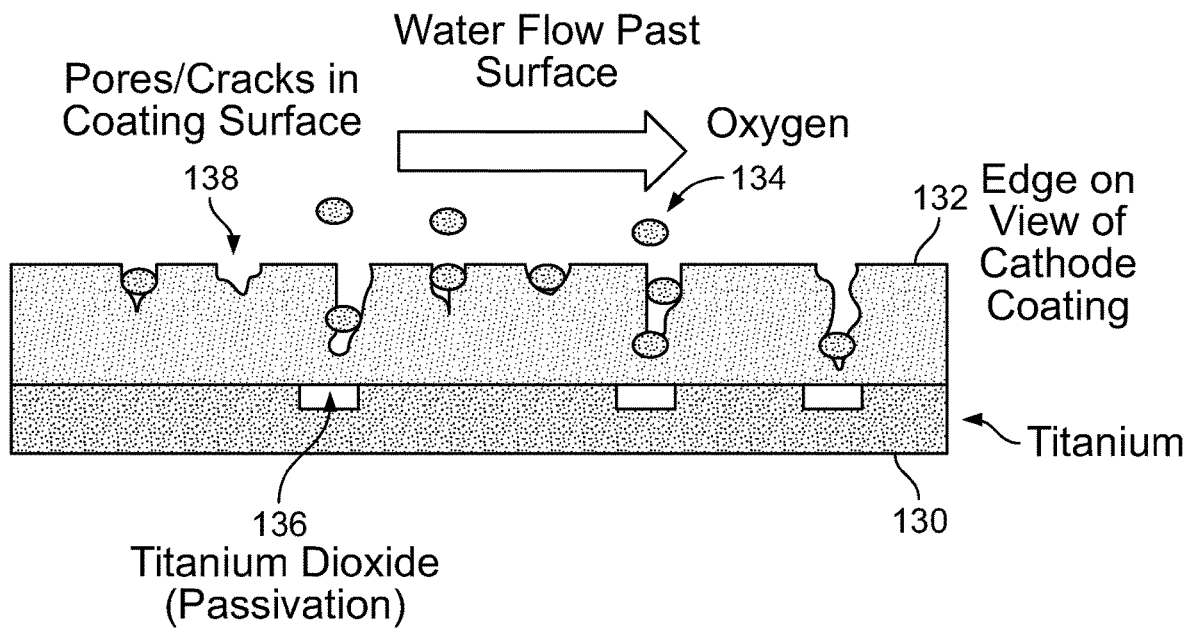
FIGS. 4A-4B are diagrams illustrating a delayed polarity reversal technique in accordance with the system of the present disclosure.
Figure 4B:
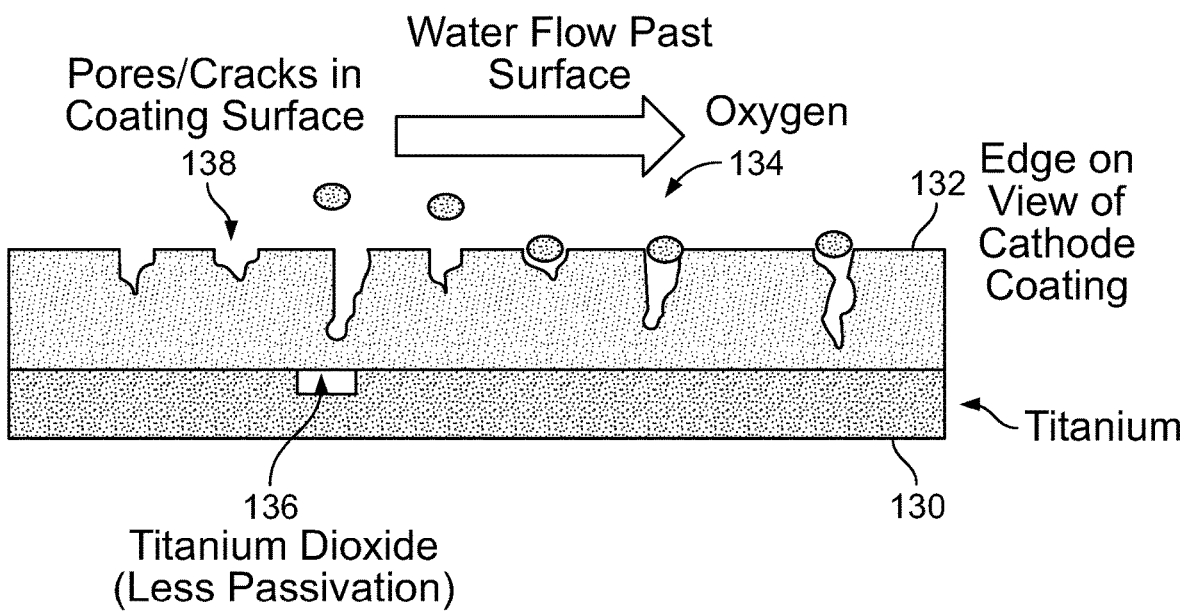

FIGS. 4A-4B are diagrams illustrating a polarity reversal delay technique in accordance with the system of the present disclosure. The polarity reversal technique allows for removal of oxygen 134 from pores/cracks 138 in the surface 132 of a cathode coating formed on a titanium electrolytic chlorinator blade 130 (which could include a layer of titanium dioxide 136). FIG. 4A illustrates the condition of the blade 130 prior to polarity reversal, and FIG. 4B illustrates the condition of the blade 130 after polarity reversal. Most salt cells are controlled in such a way that the polarity is reversed at some frequency (e.g., every 1, 2, 3, 4, 8 hours) in order to allow for self-cleaning. The very act of switching the polarity causes an anode to become a cathode and vice versa. The chemistry switches also, because an anode has an acidic surface environment (i.e., chlorine gas production) and the cathode has an alkaline surface environment (i.e., hydroxide ion production). This aids in self-cleaning as calcium scale will precipitate on the alkaline cathode but gets dissolved by the acid environment when it becomes an anode. Another aspect of polarity reversal has to do with how much time delay, if any, occurs when the polarity is switched. It is advantageous to build in a time delay between the polarity switch (as opposed to a hard switch over with no time delay) because the cathode also produces a small amount of oxygen gas 134 that can combine with the underlying titanium substrate 130 to form a passivated titanium oxide layer 136, which is non-conductive. The titanium passivation 136 (titanium converting to titanium dioxide) permanently prevents the electrode from functioning. The act of introducing a time delay is to allow the oxygen time to diffuse (convect) away so when the electrode becomes energized again there is less oxygen present to potentially form the oxide layer. A 1-minute delay between switching (with switching occurring every 3 hours) has been found to be sufficient, such that there is no detriment to overall chlorine production with a few minutes of downtime per day. It is possible that longer delays are better (e.g. 2 minutes, 4 minutes, 10 minutes) in that such delays would extend the life of the salt cell. These longer delays could be factory set or adjustable in the chlorinator control center by the end user. Alternatively, a learning algorithm can be employed whereby the monitoring of the output of the cell intelligently informs the controller as to how long it is taking for the cell to become dirty with scale. A controller can then decide as to the frequency of the polarity reversals. For example, if the cell is not scaling much (due to low hardness water), then the controller does not demand polarity reversal every "x" hours. Instead, it learns how often to reverse based on how quickly the cell is scaling.

Figure 5A:
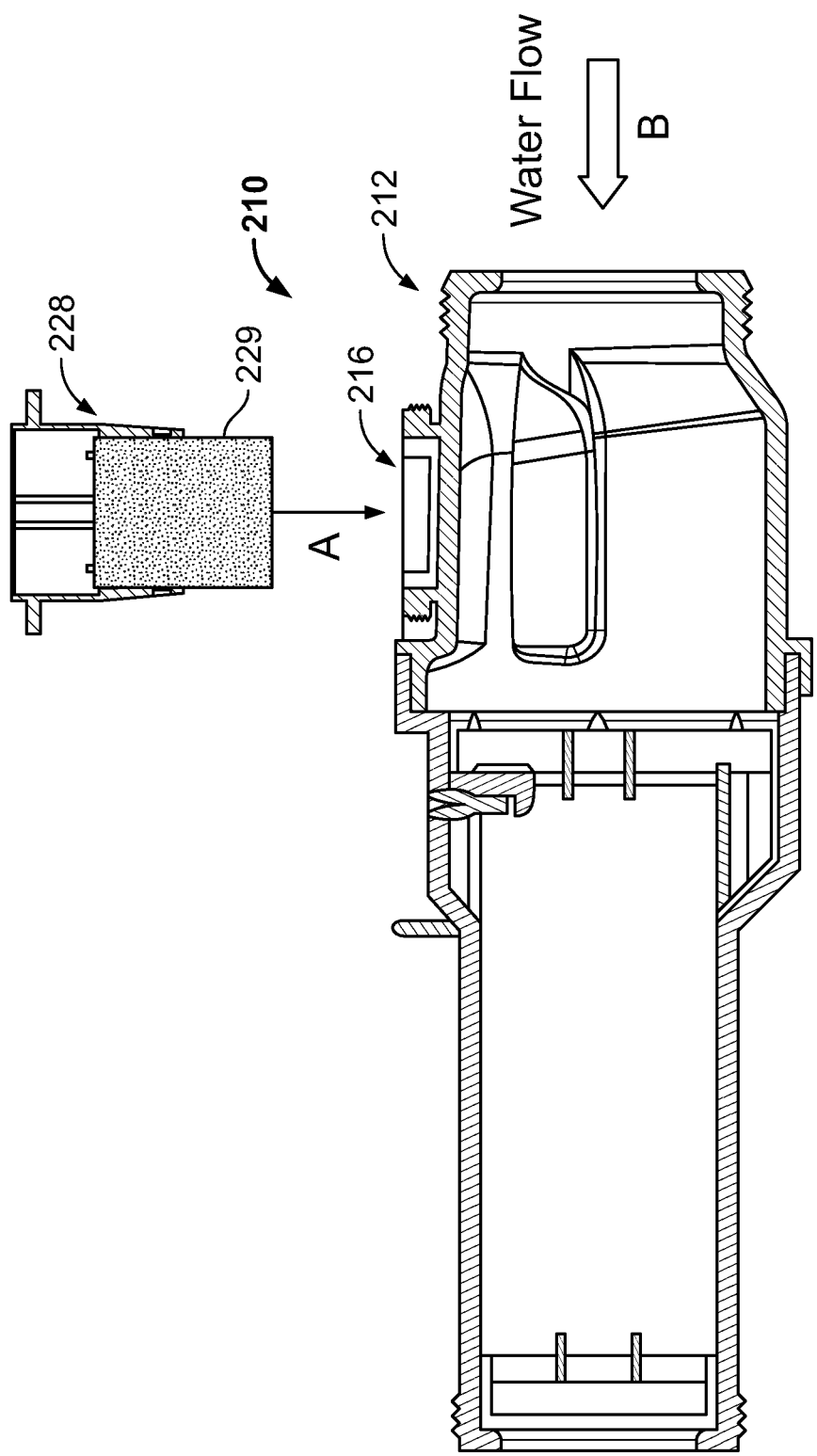
FIGS. 5A-5B are diagrams illustrating an electrolytic chlorinator having an integral sacrificial anode.
Figure 5B:
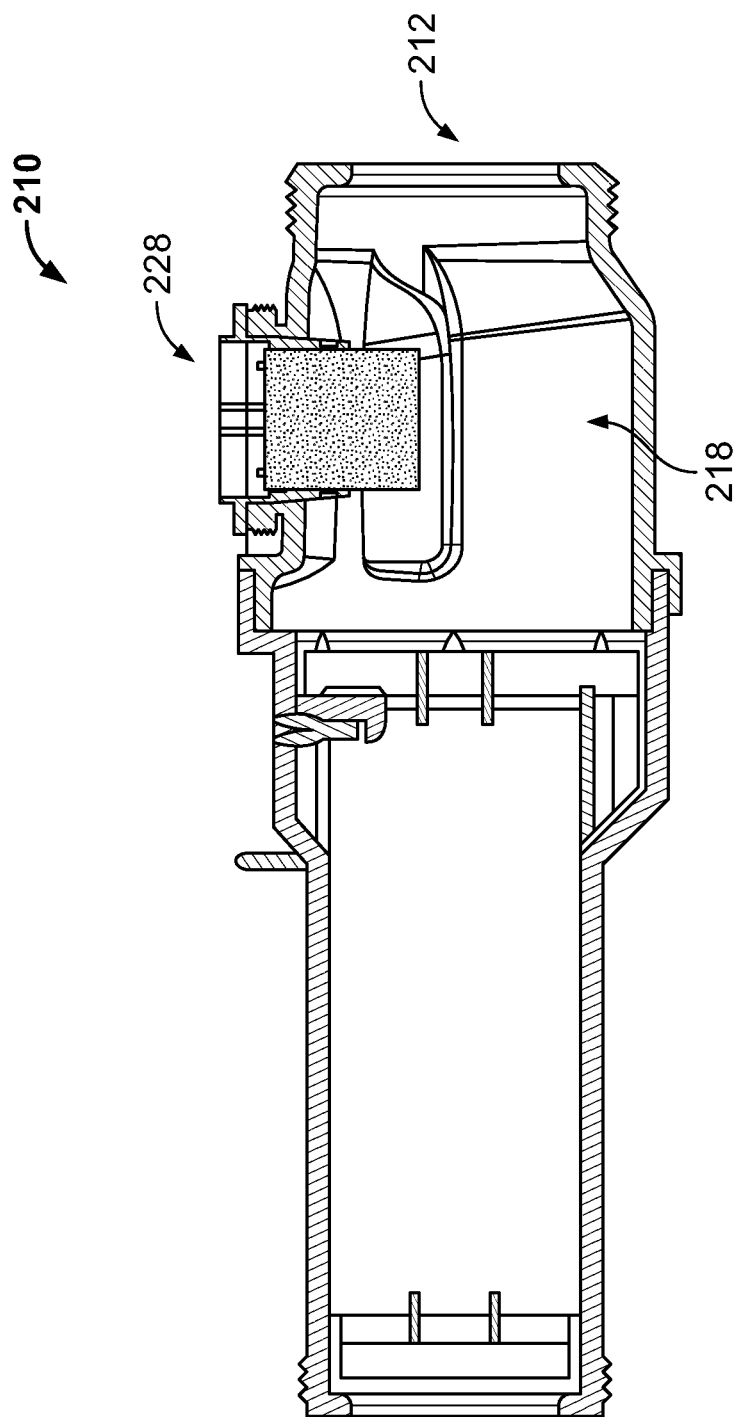

FIGS. 5A-5B illustrate another embodiment of the sanitization system of the present disclosure, wherein a chlorinator 210 includes a sacrificial anode 229. The sacrificial anode 229 could be attached to a plug 228 which inserts into an aperture 216 formed in a housing 212 of the chlorinator 210, such that the anode 229 extends into a chamber 218 formed in the chlorinator 210. Water flows into the chamber 218 in the general direction indicated by arrow B, past the sacrificial anode 229, and past electrolytic plates of the chlorinator 210. Of course, it is noted that flow direction could be reversed (in a direction opposite arrow B), if desired. Sacrificial zinc anodes can be used to help mitigate the galvanic corrosion damage done by stray currents that may exist in the water due to insufficient equipment bonding or insufficient pool grounding to earth. They can be also used to prevent a battery-like environment created between two dissimilar metals in contact with the conductive water (cathodic protection). Sacrificial anodes are wearable items and, after 6-months, 1 year, 2 years or more, the anode will need to be replaced as the zinc will have dissolved away. Zinc is used as sacrificial anodes in marine application extensively (e.g. to protect the hull of ships in salt/brackish water). Zinc happens to have some algistatic properties as well so its dissolution is desirable not only from the sacrificial anode standpoint but from the aspect that it provide an algistat to the pool water.

Figure 6A:
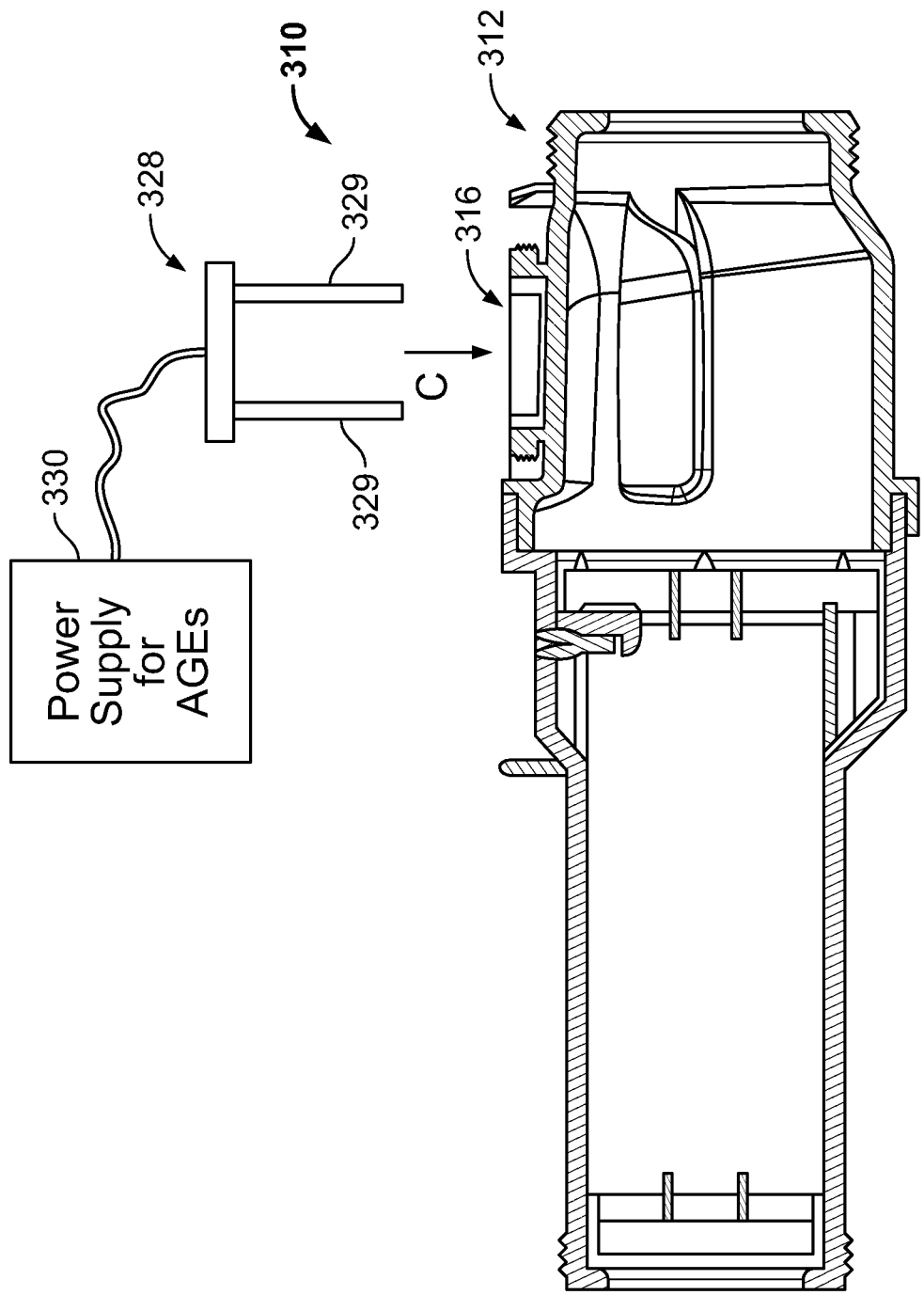
FIGS. 6A-6B are diagrams illustrating an electrolytic chlorinator having an integral, electronically-controlled acid generator.
Figure 6B:
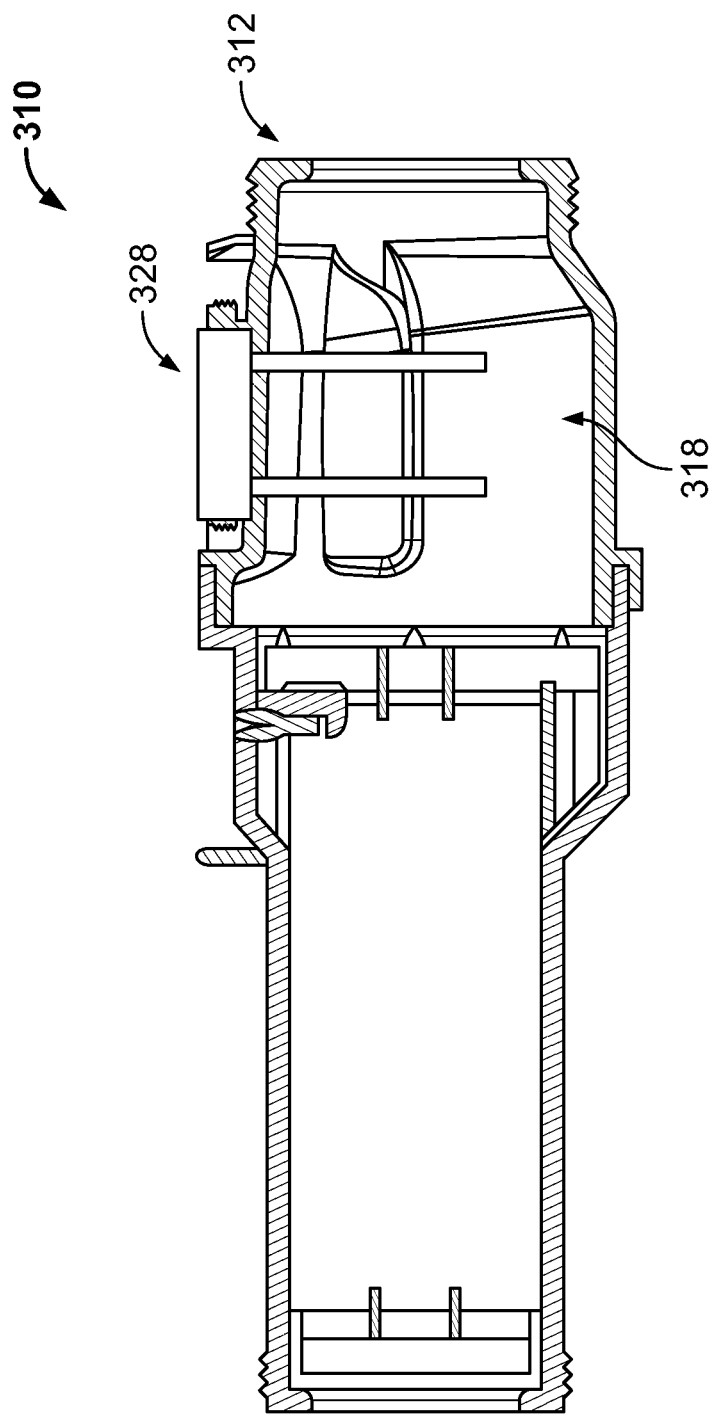

FIGS. 6A-6B illustrate another embodiment of the sanitization system of the present disclosure, wherein a chlorinator 312 includes an integrated acid generator 329. The acid generator 329 could be attached to a plug 328 which inserts into an aperture 316 formed in a housing 312 of the chlorinator 310 (in the general direction indicated by arrow C), such that the acid generator 329 extends into a chamber 318 formed in the housing 312 of the chlorinator 310. The acid generator 329 could be powered by a power supply 330 in electrical communication with the anodes 329. Salt chlorine generators naturally cause an increase in the pH of the water due to the net chemical reaction: $2NaCl+2H_2O \rightarrow Cl_2 + 2NaOH + 2H_2$. To counteract the pH increase due to the sodium hydroxide production (i.e. NaOH), the acid generator 329 generates an acid (i.e. protons—aka $H^+$—aka $H_3O^+$), and could be formed from a pair of electrodes that can fit inside the chlorinator 310. The acid generator 329 operates when the salt cell is operating in order to neutralize the pH change. Alternatively, or additionally, the acid generator 329 can be turned on just prior to the pump so the cell can be soaked in acid and cleaned of scale. Alternatively, or additionally, the acid generator 329 can be turned on after the pump shuts off so the cell can be soaked in acid and cleaned of scale. The acid generator 329 can be intelligently matched to the salt cell operation so that the NaOH is precisely neutralized. The acid generator 329 can also operate independent of the cell to lower the pH of the pool water when desired.

Figure 7:
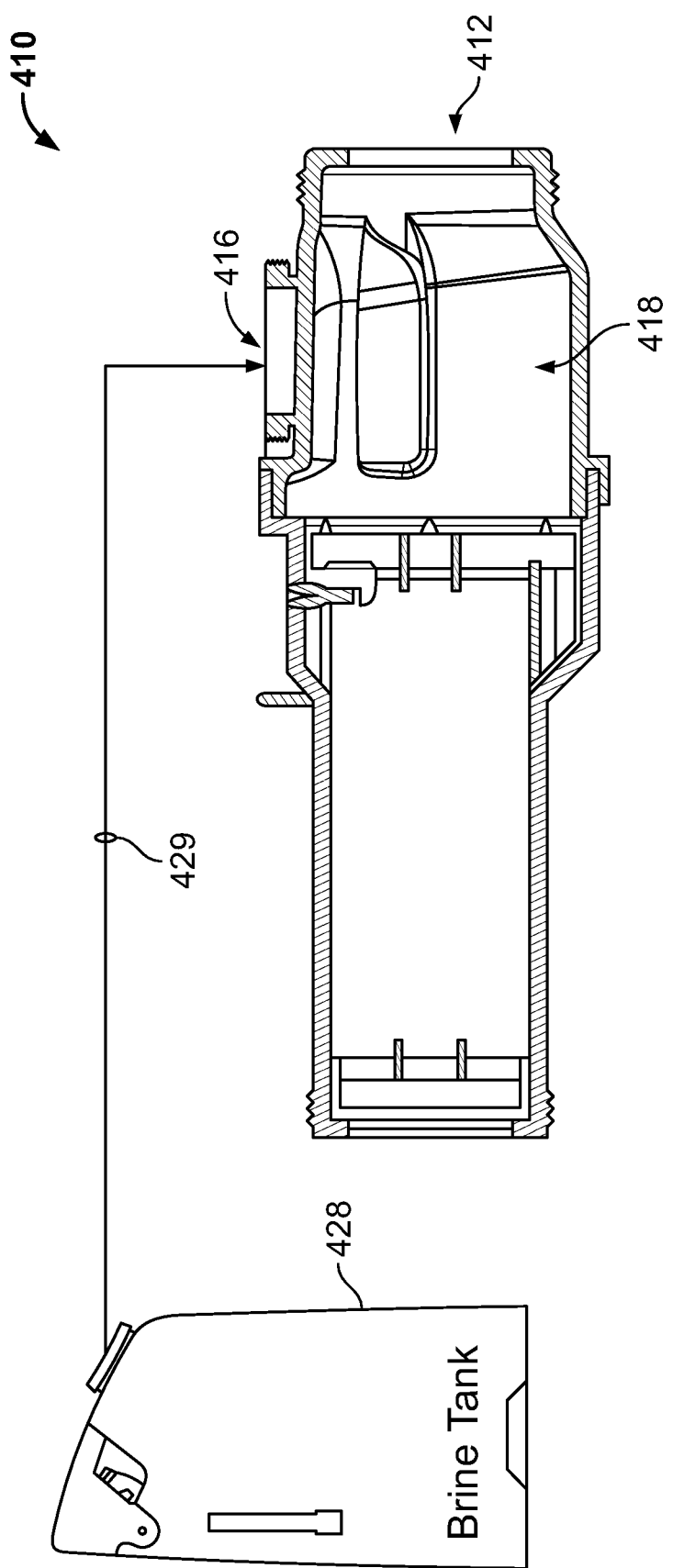
FIG. 7 is a diagram illustrating an electrolytic chlorinator having a brine tank for shocking and/or superchlorinating pool/spa water.

FIG. 7 is a diagram illustrating another embodiment of the sanitization system of the present disclosure, wherein a chlorinator 410 is provided which is fed by a brine tank 428 in fluid communication with the chlorinator 410 via a tube 429 to provide for superchlorination when needed. The tube 429 is in fluid communication with a port 416 formed in a housing 412 of the chlorinator 410, such that brine is periodically injected into a chamber 418 of the chlorinator 410. Pools and spas occasionally require a shock of chlorine (aka—superchlorination) to oxidize contaminants (e.g. organics, dead bacteria, metals, combined chlorine)). Salt chlorine generators generally do not make good superchlorinators because they generate chlorine too slowly. For example, a typical salt generator will make 1-2 lbs of chlorine per day but the superchlorination of a pool calls for raising the chlorine level to 10 ppm rapidly. A 40,000 gallon pool would need about 4 lbs of chlorine to raise it to 10 ppm (from 0 ppm) but that cannot be done quickly with a salt system. In order to enable the salt system to produce more chlorine, a higher salt level can be used. Raising the salt level in the entire pool would be undesirable. The brine tank 428 provides a high salt concentration into the salt cell so the cell can make more chlorine without needing to raise the salt level of the entire pool. The brine tank 428 (containing dissolved salt at a concentration similar to ocean water—30,000 ppm—or even higher—up to saturation level of salt in water at room temperature) is fed directly into the salt cell while the flow rate through the cell is reduced (this is to keep from diluting the introduced salt solution yet allowing flow to carry away chlorine gas). The higher salt concentration will allow the salt cell to make more chlorine and the salt cell can then serve as a means of superchlorinating the pool/spa.

Figure 8:
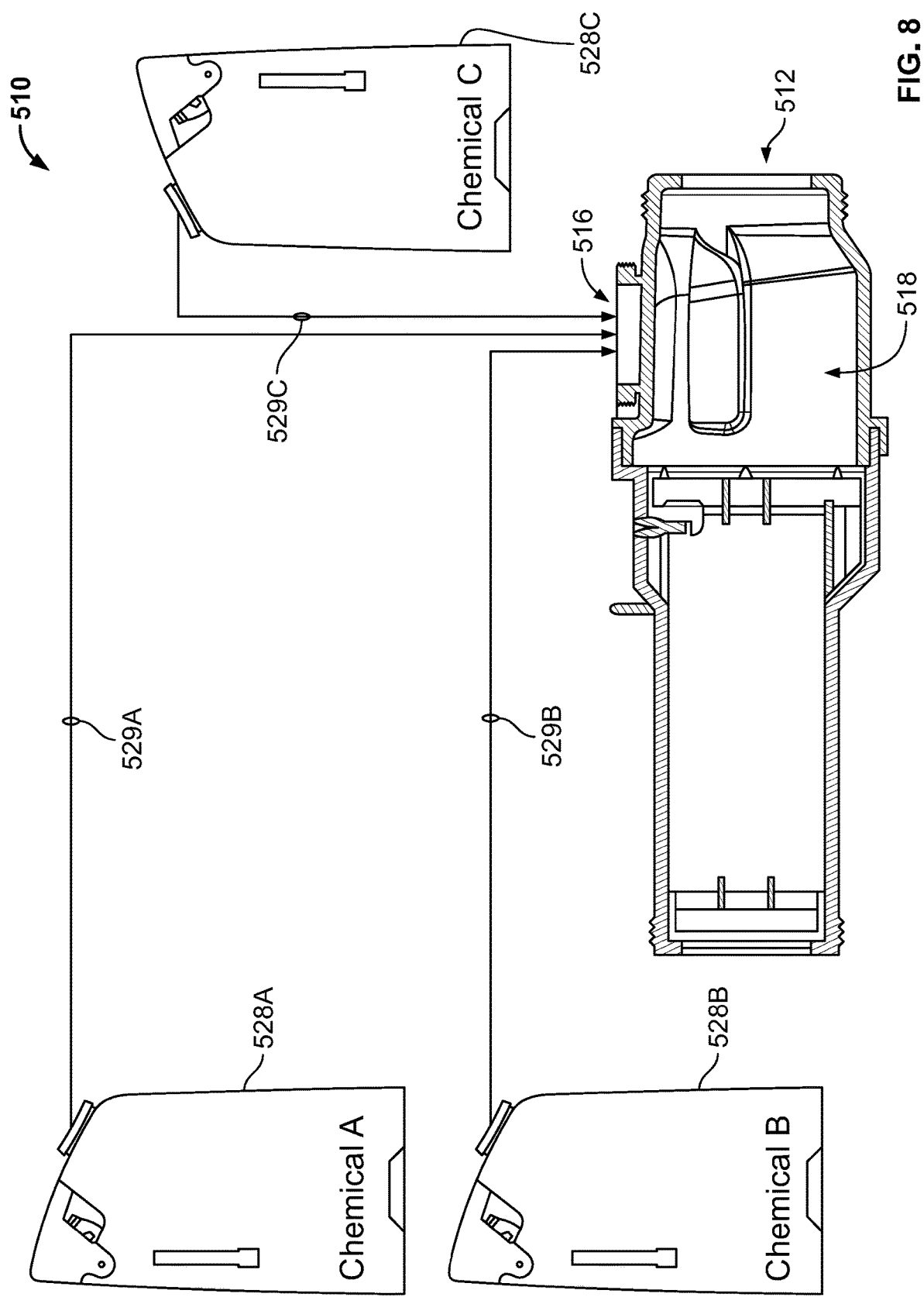
FIG. 8 is a diagram illustrating an electrolytic chlorinator having a plurality of chemical tanks and/or feeders for periodically introducing chemicals into the chlorinator.

FIG. 8 is a diagram illustrating another embodiment of the sanitization system of the present disclosure, wherein a chlorinator 510 is in fluid communication with a plurality of chemical feeders 528a-528c via fluid lines 529a-529c. The fluid lines 529a-529c inject fluids from the feeders 528a-528c into a chamber 518 formed in the housing 512 of the chlorinator 510. Many different chemicals are available to add to pools to control water quality issues such as high metals content, high phosphate levels, high organic load, high or low pH, high or low alkalinity, low cyanuric acid, low hardness, foaming, etc. All of these chemicals can be introduced in liquid form into the port 516 of the electrolytic chlorinator 512. The chemical types and their functions could include, but are not limited to, the following:

| | |
|---|---|
| Sequesterants | Remove metals |
| Chelating agents | Bind metals, bind cations (e.g. calcium) |
| Defoamers | Reduce foaming |
| Fragrances | Improve water odor |
| Acid (e.g. muriatic) | Lower pH, lower alkalinity |
| Sodium carbonate solution | Raise pH |

| | |
|---|---|
| Sodium bicarbonate solution | Raise alkalinity |
| Cyanuric acid | Chlorine stabilizer |
| Calcium chloride solution | Increase water hardness |
| Sodium bisulfite solution | Reduce excess chlorine levels |
| Sodium bromide solution | Algicide |
| Hydrogen peroxide | Oxidizer |
| Metals solution (e.g. silver nitrate, copper sulfate, zinc nitrate) | Algistat, algicide, bacteriostat, bacteriocide |
| Chemical that acts as solar blanket on surface of the water | Solar blanket-keeps heat in water and prevent heat escape |
| Enzyme solutions | Eats organic matter |
| Phosphate removers | Reduces phosphate levels that can promote algae |
| Algicides | Prevent or kill algae |
| Liquid Chlorine | Sanitizer and oxidizer |

It is noted that a manifold could be constructed so that multiple feed tanks can feed into the same port 516 on the chlorinator 512.

Figure 9:
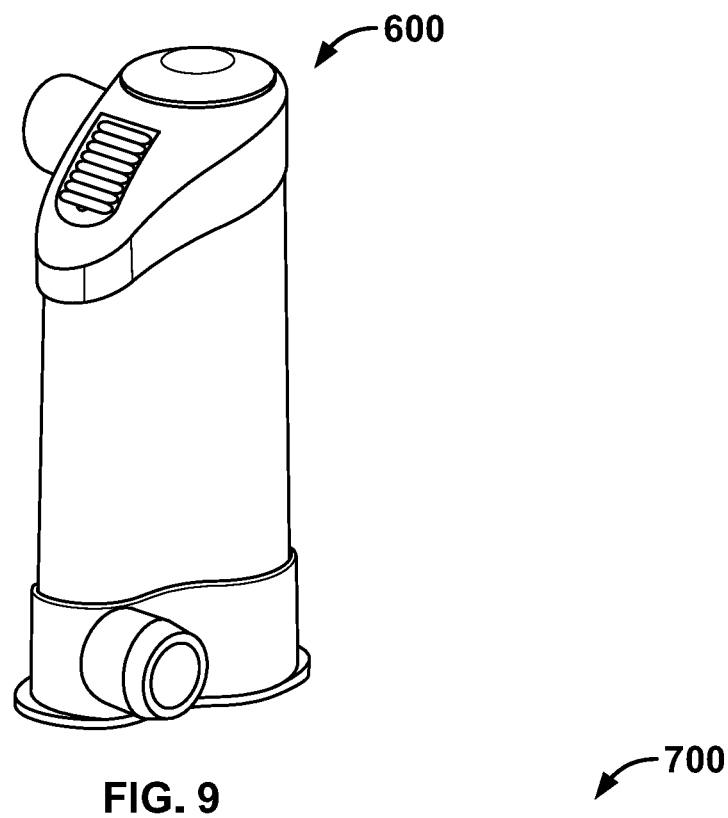
FIG. 9 is a diagram of a conventional ultraviolet sanitizer.
Figure 10:
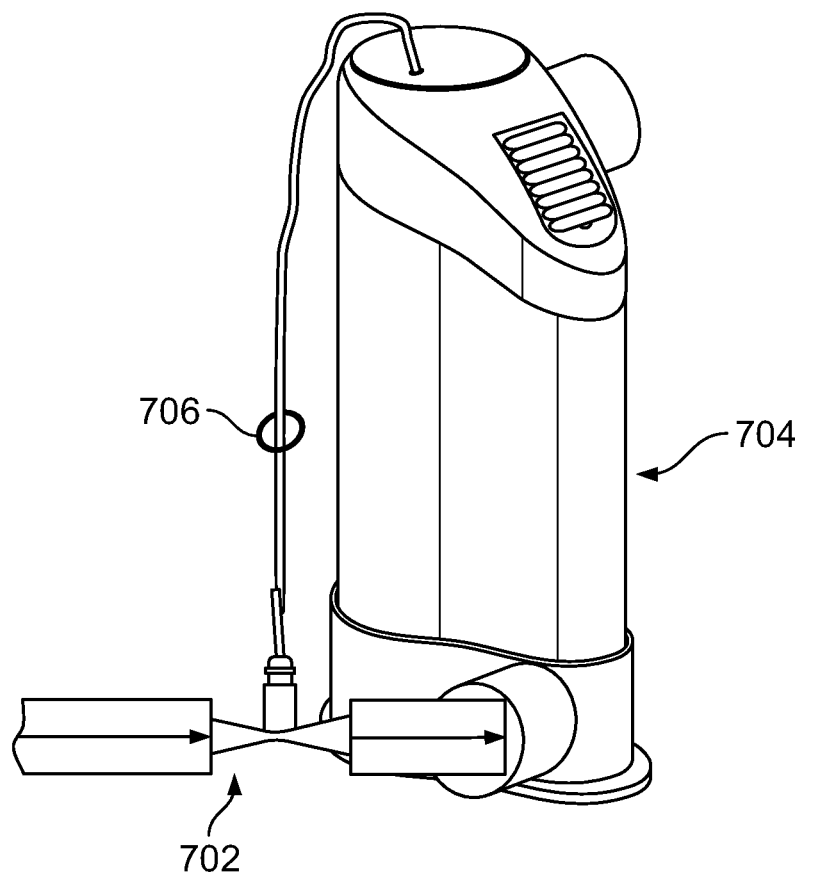
FIG. 10 is a diagram of a conventional ultraviolet/ozone sanitizer.
Figure 11:
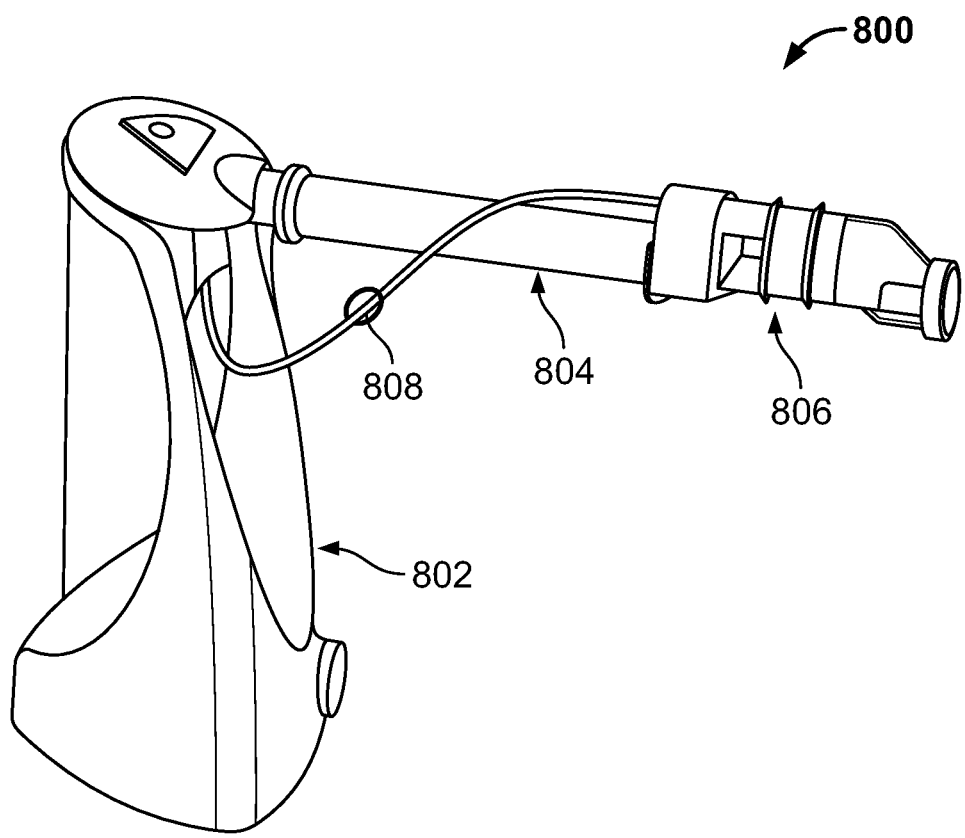
FIGS. 11-12 are diagrams of an ultraviolet/ozone sanitizer and electrolytic chlorine generator in accordance with the present disclosure.

FIG. 9 is a diagram illustrating a conventional ultraviolet (UV) sanitization system, indicated generally at 600. UV, Ozone and salt chlorine generation systems are all well-known methods to sanitize pool water. These technologies can be employed individually on a pool or spa in combination with each other. Some systems have been reported that combine UV and ozone into a single system using a UV lamp that serves as both the source of UV light for water treatment and ozone generation for water treatment. One example of such a system is shown in FIG. 10 at 700, which depicts an ultraviolet sanitizer system 704 that has ozone generation capabilities. Ozone is generated by the ultraviolet light of the sanitizer system 704, is siphoned via a tube 706, and is fed into pool/spa water to be treated using a venturi 702. Such systems (shown in FIGS. 9 and 10) could be further modified to include a salt chlorine generator, as indicated at 800 in FIG. 11. Such a system 800 includes an ultraviolet and/or UV/Ozone generator 802, and a salt chlorine (electrolytic) generator 806 in fluid communication with the generator 802 by piping 804 and/or tubing 808. It is noted that the salt cell (i.e. chlorine generating electrodes) can be placed directly inside the UV and/or UV/Ozone vessel, if desired. The advantages may include a smaller equipment footprint on the pool pad and the use of a single electronic controller. Since neither UV nor ozone can be used as a stand-alone sanitizer due lack of a lasting chemical residual, chlorine is required with either a UV or UV/Ozone system—hence, integration into a single product makes sense.

Figure 12:
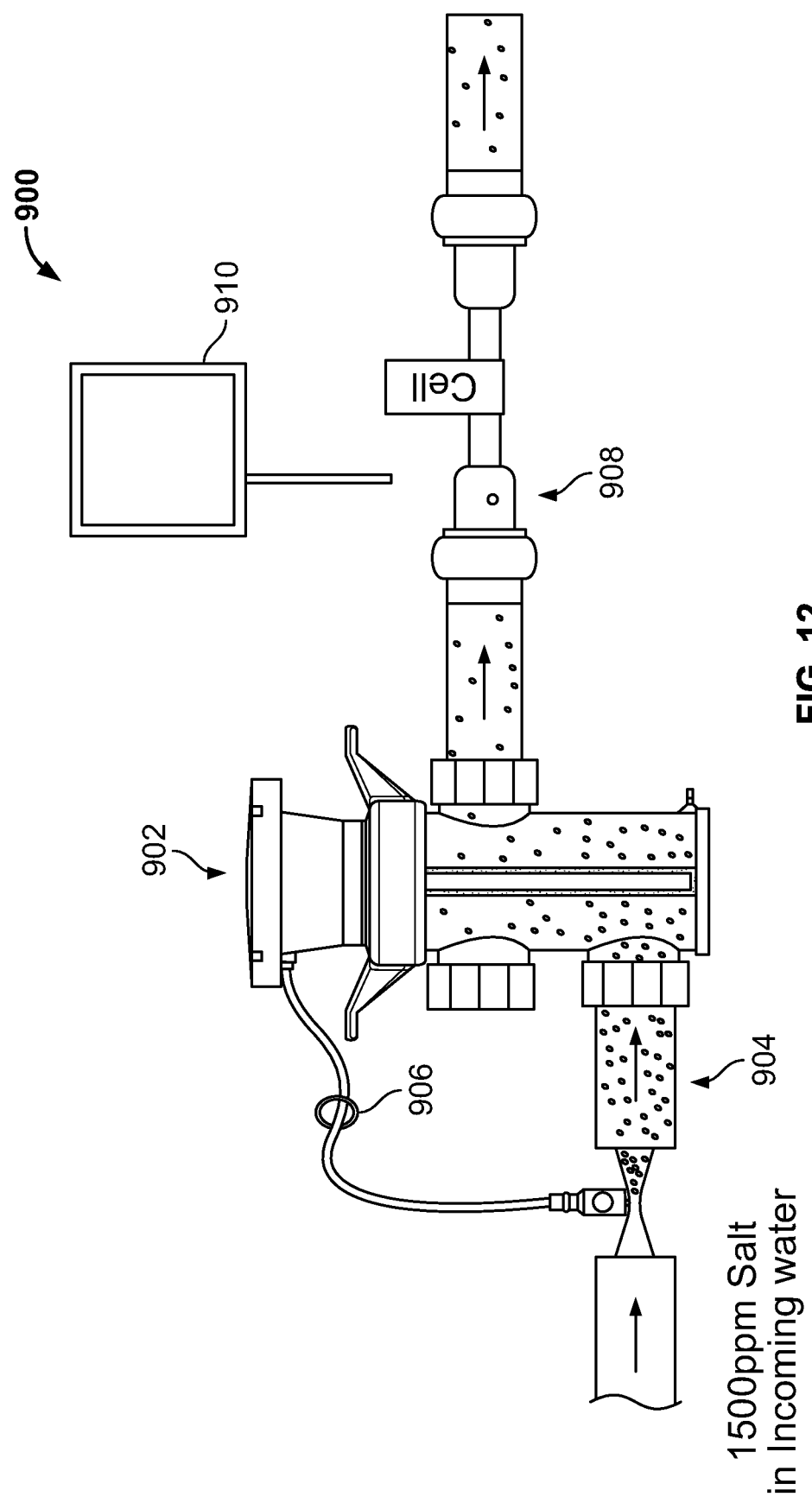

FIG. 12 is a diagram illustrating another embodiment of the sanitization system of the present disclosure, indicated generally at 900. In this embodiment, the sanitization system 900 includes an ultraviolet/ozone (UV/O3) sanitization system 902 in fluid communication with an electrolytic chlorinator 908. The electrolytic chlorinator could be controlled by an electronic controller 910. The UV/O3 sanitization system 902 could include a venturi assembly 904 which feeds ozone into water to be treated. Such ozone could be supplied via a tube 906 which draws ozone generated from ultraviolet lamps in the system 902. A big benefit of using a UV and/or a UV/ozone and/or an Ozone generator with a chlorine source for pool and or spa water treatment is that the amount of chlorine needed can be much less—on the order of 50% less. Due to the lower chlorine output needed, the end user has at least 2 options when paring these systems with a salt water chlorinator: reduce the operating time of an existing salt system (say by 50% for example) and, as a result, extend the duration of the use of a salt cell by a factor of 2, or, pair the UV, UV/Ozone, or Ozone system with a LOW SALT chlorine generator. The lower salt level will: 1) reduce the chlorine output of the salt chlorine generator; and 2) will lower the risk for corrosion of pool decking, pool equipment and poolside furniture. LOW SALT is defined as being less than 2500 ppm, preferably less than 2000 ppm and most preferably less than 1500 ppm.

Figure 13A:
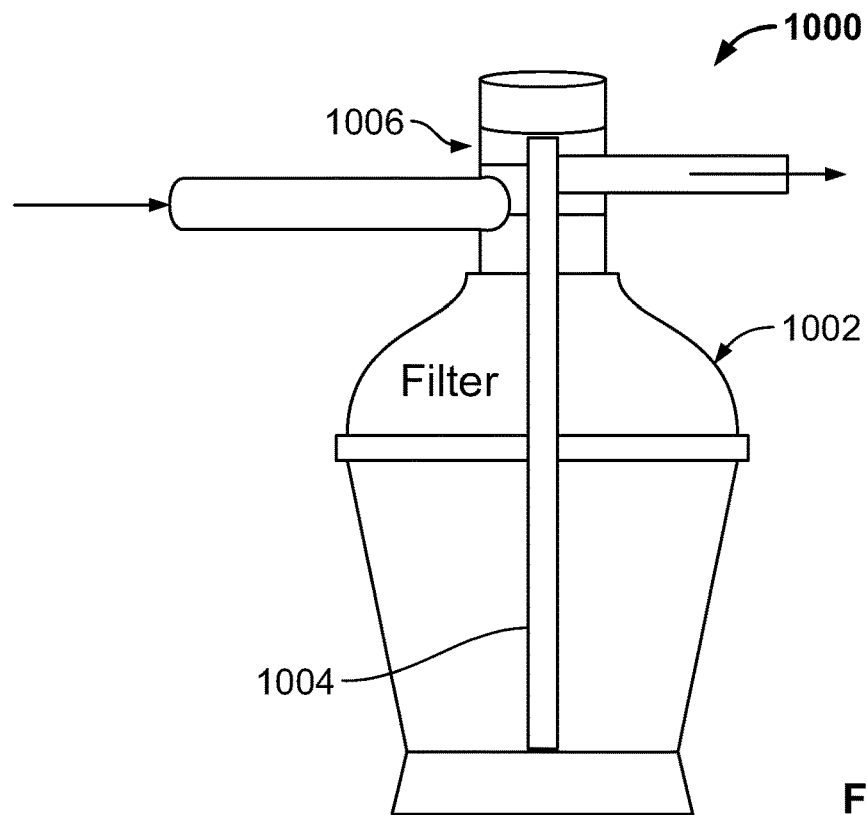
FIGS. 13A-13B are diagrams illustrating filtration systems having integral UV sanitizers in accordance with the present disclosure.
Figure 13B:
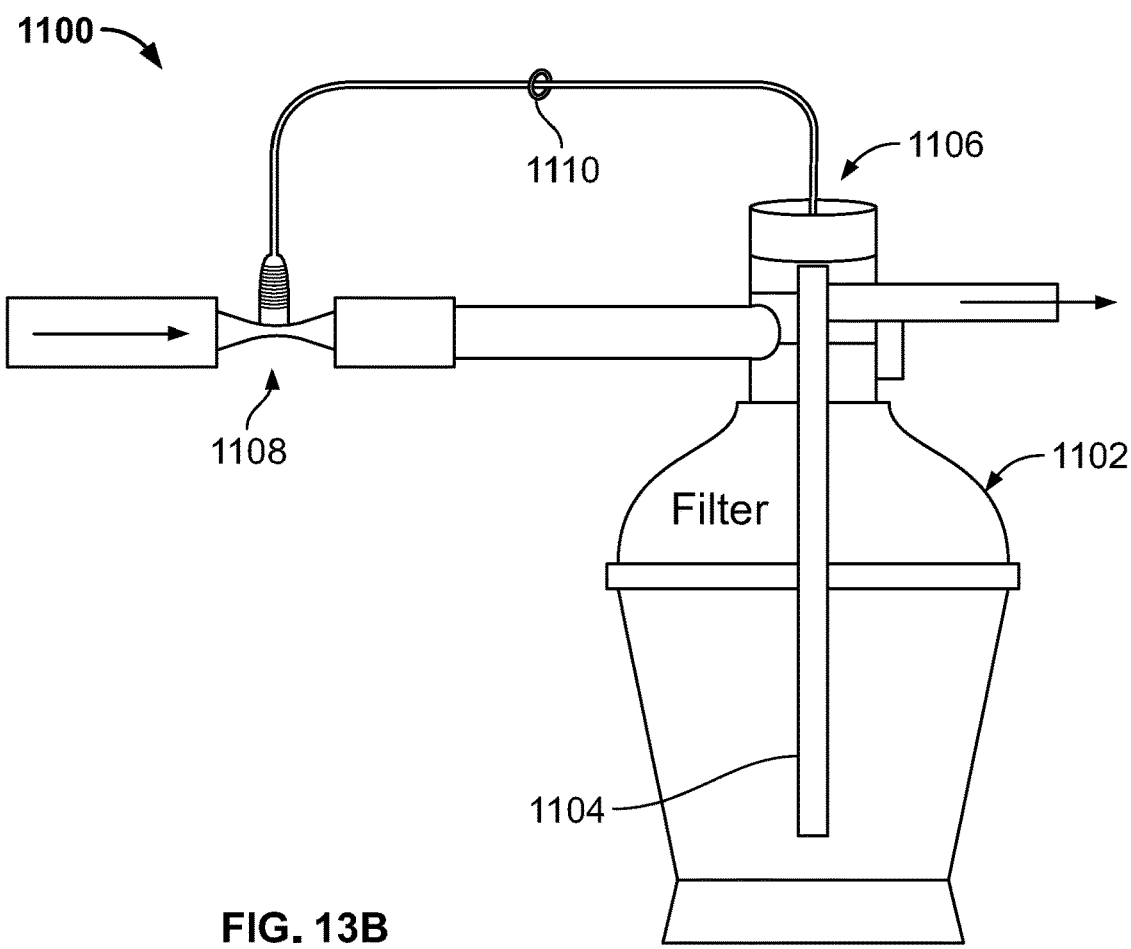

FIGS. 13A-13B are diagrams illustrating another embodiment of the sanitization system of the present disclosure. As shown in FIG. 13A, the system 1000 includes a filter 1002 and an ultraviolet sanitization system 1004 positioned within the filter 1002. A manifold 1006 could control water flow through the filter 1002, and could provide a mounting point from which the ultraviolet sanitization system is suspended. As shown in FIG. 13B, the system of FIG. 13A is expanded (indicated generally at 1100) to also include an ozone feeder system that includes a venturi assembly 1108 and a tube 1110 for feeding ozone into water to be filtered. The ozone could be supplied by an ultraviolet assembly 1104 positioned within the filter 1102 and suspended from a manifold 1106.

Manways or 'manhole covers" can be placed on filter housings for easy access to media servicing or replacement (e.g., as in sand filters). The manway can serve as the access point for the insertion of one or more UV lamps. The only requirement of the final system is that the water is filtered prior to passing the UV lamps—this is because UV works best when the water is clear. Furthermore, filtered water is less likely to foul the glass sleeve that is placed around the lamp.

Figure 14B:
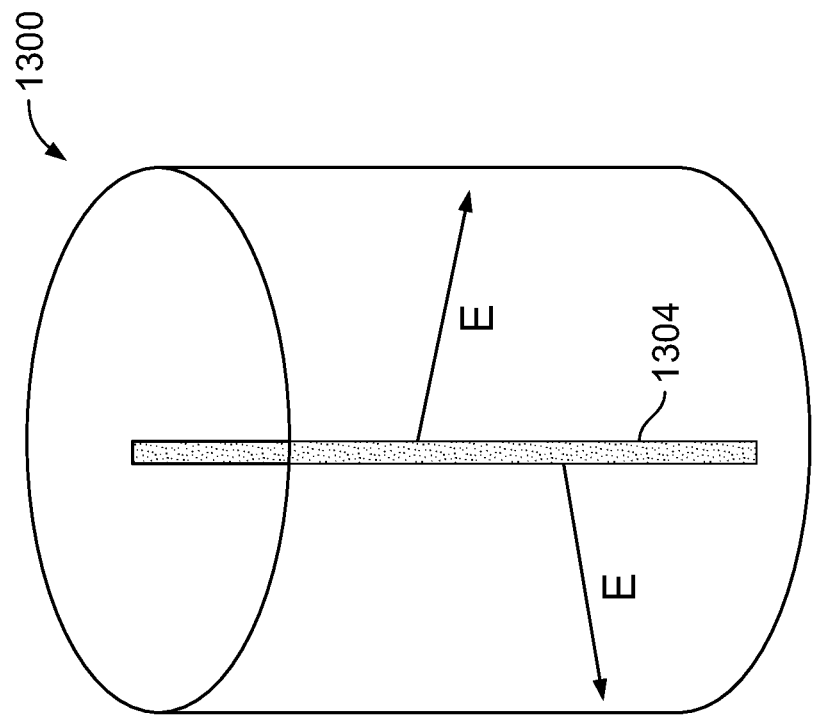
FIGS. 14A-14B are diagrams illustrating reflective inner surfaces for UV sanitizers.
Figure 14A:
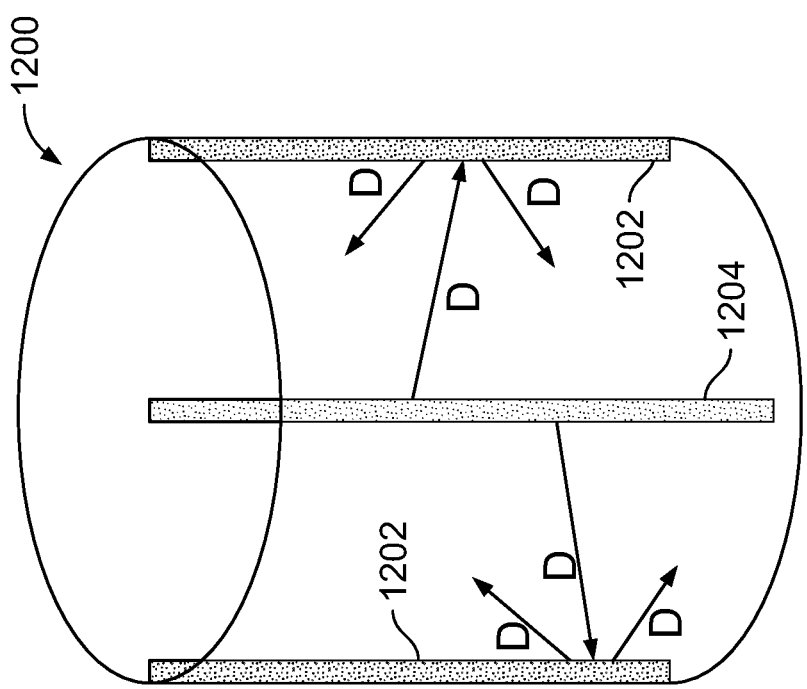

FIGS. 14A-14B are diagrams illustrating ultraviolet sanitization systems which include reflective liners. As shown in FIG. 14A, the sanitizer 1200 includes an ultraviolet lamp 1204 and reflective liner 1202 which reflects light into the sanitizer 1200 as indicated by arrows D. A conventional sanitizer 1300 is shown in FIG. 14B, which lacks a reflective liner. As can be appreciated, only direct light emanating from the lamp 1304 is available to sanitize water, as indicated by arrows E. UV reflective surfaces allow a portion of the UV light to return to the water column where it can provide additional benefit in the way of microbial inactivation. Some UV reflective materials that could be utilized for the liner 1202 are listed below:

| Material | UV Reflectivity |
|---|---|
| Plastic | 10% |
| Polished stainless steel (SS) | 30% |
| Polished aluminum | 60% |
| Teflon (PTFE) | >99% |

Figure 15:
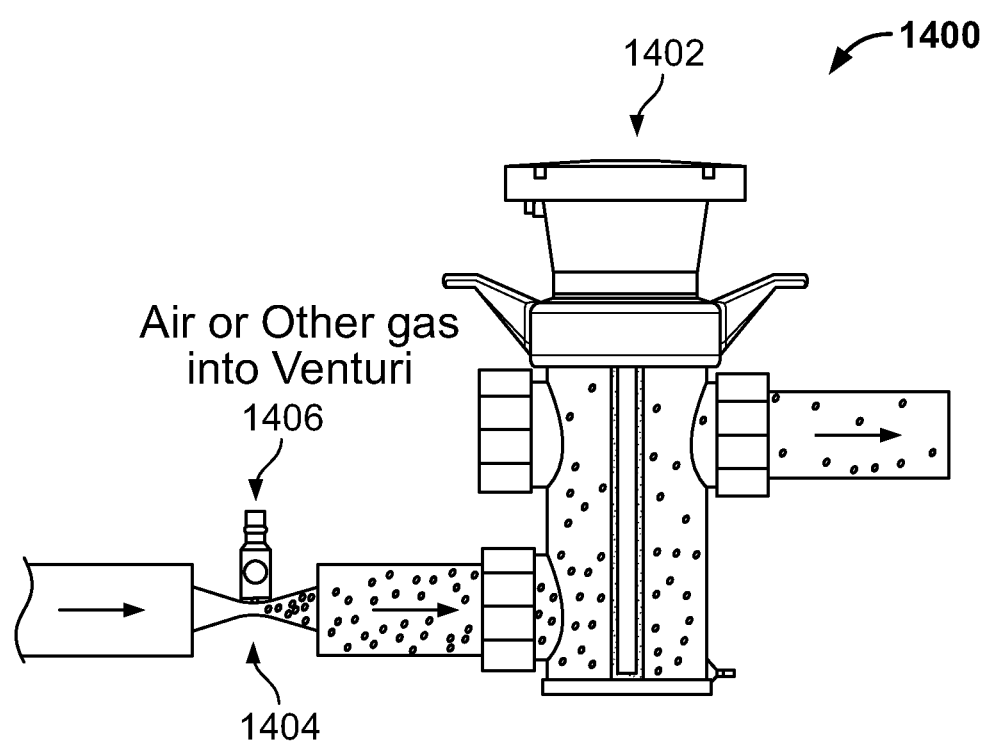
FIG. 15 is a diagram illustrating a UV/Ozone sanitizer having bubble generation capability.

No system exists whereby a highly reflective coating (i.e. greater than polished SS) has been added to the vessel wall of a UV/ozone water treatment system. Such a system has the benefit of the returned UV light to the water column where it can convert ozone to hydroxyl radicals—or at the very least—destroy the ozone so it does not return to the pool or spa where off-gassing of the ozone can harm bathers FIG. 15 is a diagram illustrating another embodiment of the sanitization system of the present disclosure, indicated generally at 1400, which introduces air or gas bubbles into water to be treated. In this embodiment, the sanitization system 1400 includes a combined UV/O3 sanitization system 1402, a venturi assembly 1404, and an external supply 1406 of air or another gas for sanitizing water being fed into the system 1400. The addition of an air bubble (irrespective of the gas composition in that bubble), causes the UV light to reflect/diffract off the bubble surface thereby increasing the mean path length through the water column before the UV hits the reactor wall where the majority of its energy is lost as heat.

Figure 16:
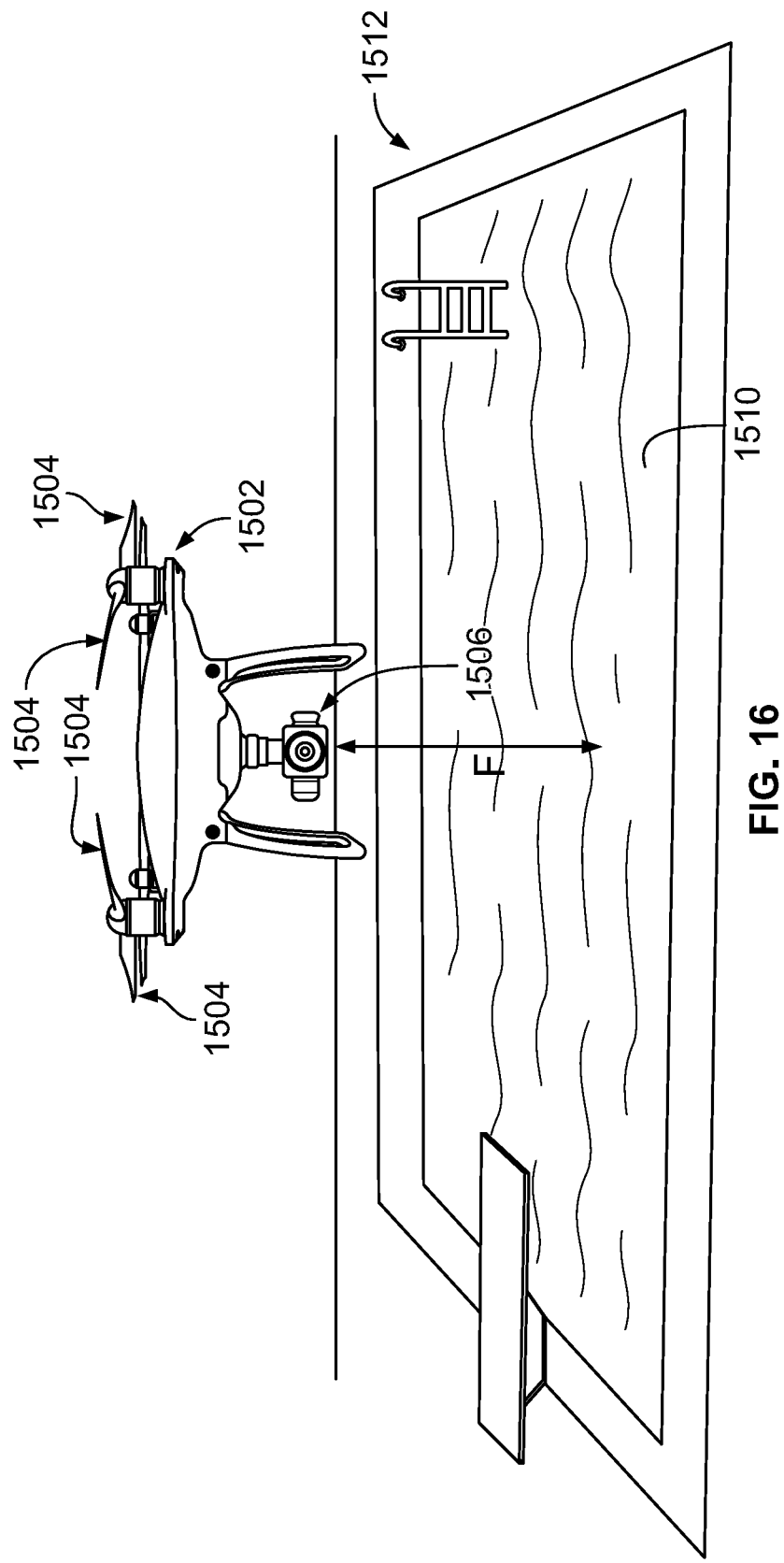
FIG. 16 is a diagram illustrating a system for obtaining samples of pool/spa water using unmanned aerial vehicles (drones).

FIG. 16 is a diagram illustrating another embodiment of the sanitization system of the present disclosure, which includes an unmanned aerial vehicle (UAV) or drone 1500 that can fly toward a body of water such as a pool or spa 1512 (in the direction indicated by arrow F) and periodically obtain a sample of water 1510 from the body of water. The drone 1500 could include a body 1502, propellers 1504 for propelling the drone 1500, and a water sampling device 1506 for obtaining samples of the water 1510. The drone 1500 could transport the sample of water to a testing facility whereby the water is tested for various characteristics such as water quality, pH, chlorine levels, bromine levels, etc. Alternatively, the drone 1500 could include sensors for automatically testing such characteristics on-board the drone 1500, so that the drone need not fly to a testing facility.

For the vast majority of pool and spa owners, a proper water analysis is conducted by the end user bringing a water sample to a local retail or service store where specialized equipment is available to evaluate the water quality. Water quality parameters such as pH, free chlorine, total chlorine, combined chlorine, bromine, calcium hardness, total alkalinity, total dissolved solids, cyanuric acid, phosphate levels, metals (such as Fe, Mn, Cu and Ag), and salt (i.e. sodium chloride), are commonly measured. Many of these measurements are beyond the scope (and affordability—as analytical equipment can be expensive for a homeowner) of what is available to the consumer to perform at their home. Most consumers, if they make measurement themselves will use simple test strips or simple dropper kits. The tests trips measure free chlorine, total chlorine, pH, total alkalinity, total hardness, cyanuric acid and pH whereas the dropper kits typically are limited to pH and free and total chlorine. The inconvenience of bringing a water sample to a store can be alleviated by the use of the drone 1500 which flies to the location of the pool and/or spa and gathers a water sample. The drone is outfitted with a means to gather and store a volume of water, typically 2 mL or more, preferably 5 mL or more, and most preferably 10 mL or more. The collected water sample can be brought back to a water testing location for analysis or, given sufficient onboard sensors, the drone could analyze the water, including temperature, at the point of pick up. In either case, the results can be sent to the homeowner or a service company for immediate action should any of the water quality parameters fall outside of recommended guidelines. The drone could be outfitted with GPS or equivalent to locate the body of water. Furthermore, the drone can have onboard sensors, protected from the elements within its housing, that detect whether the pool or spa has a cover on it and whether or not there are active bathers in the water. In the event of active bathers, an audible alarm could warn of the impending water landing, or alternatively, the drone can 'reschedule' its visit or manage to descend without approaching closer than 10 feet to a bather. Finally, the drone can have communication capability (WiFi or other) that allow it to be manually guided or rerouted as deemed necessary by the sending party. We can imagine that the sender is managing the flight of the drones in a manner similar to the tracking of airline flights by air traffic control. Additionally, the onboard communication of the drone can alert the end user (by text or email) when it intends to be at their location and can then communicate the results of its findings. On-board sensors could also be part of the drone that enable it to test turbidity and sense physical debris in the water, using cameras for example, so it can alert appropriate parties as to the need for added filtration or filtration maintenance as well as pool cleaning services. The drone could direct an automatic pool cleaner to certain top, side and bottom locations for debris removal as well as instruct a pool automation system on filtration cycle management, chlorination output, heater control, etc.

Additional features of could be provided in accordance with the present disclosure as follows.

If a salt chlorine generator output varies with salt level, water temperature, current supplied or other external variable, then a fixed amount of chlorine per day can be maintained by sensing chlorine generator amperage versus the amount of chlorine generator runtime and then keeping the filter running (or intentionally shortening its on-cycle) to match the targeted daily chlorine dosage. A system could be provided wherein chlorine generator production rate is modified with water temperature to match higher chlorine demand in hotter water versus lower chlorine demand in colder water. Such a system could combine amperage utilization by chlorinator with pump schedule to predict chlorine dose provided by the schedule. Further, such a system could modify chlorine dosing (salt system or liquid or tablet chlorine feeder) with weather reports and geographies (e.g. hot in AZ combined with wind creates more dust in pool; anticipate temp at night to assess overall chlorine demand).

In a salt chlorine generator, a system could be provided wherein the generator modifies polarity reversal rates of the chlorine generator based on water hardness, water temperature, age of salt cell and flow rate.

Various smart sensing and control techniques could be implemented in accordance with the present disclosure. For example, such techniques could involve the use of predictive trends of water quality data (e.g. pH trend line) to determine dosing regimen rather than simple timeout features (Example of old method: Acid feeder is activated due to high pH. After several hours the pH target still not met so a timeout alarm is used to stop what may be a bad pH probe and overdosing of acid. Example of new method: Acid feeder is activated due to high pH. After several hours the pH target still not met but the pH trend line is going as expected and so dosing continues). Such a method eliminates false alarms and inconvenient timeouts. Additionally, the system could modify/compensate ORP set point with measured pH value. Since ORP drops as pH increases, a potential exists to continue adding chlorine when in fact ORP only dropped due to pH and not due to insufficient chlorine. The issue of falling ORP with rising pH is currently problematic with salt chlorinators managed by ORP sensing because the pH will rise as the chlorine generator operates, causing a lowering of the ORP and the potential for the ORP not to hit its set point, calling for more chlorine when in fact there is plenty. Still further, the system could modify/compensate ORP set point with sunlight. UV/visible rays have a pronounced effect on ORP if cyanuric acid is used. For example, at the same chlorine level, water exposed to darkness will have a higher ORP than the same body of water exposed to sunlight (because cyanuric acid will bind the chlorine more tightly in the sun—has to do with the binding strength between the chlorine molecule and cyanuric acid molecule as a function of UV/visible light). The system could also be embedded with a reminder system in the equipment (chlorinator, pump, etc.) to recommend manual water tests. A calculator/wizard could be used to recommend ORP set points and chlorine dosing based on manual water tests. Further, the system can calculate acid needed to offset pH rise when using a salt chlorinator as a function of water chemistry parameters, chlorinator runtime, geography and weather reports. For example, the pH rise in a given week/month associated with specific chlorinator usage can be predicted for a given pool given its volume and water chemistry. If however, acid rain occurs, the need for additional acid may be nil in any given period. Other water parameters that could be sensed include alkalinity, cyanuric acid levels, and calcium hardness levels.

Additionally, further improvements can be made to salt chlorinators in accordance with the present disclosure, as follows. Salt chlorine generators typically are designed to shut off when the water flow stops. That is, they are controlled by a flow switch that triggers the shut off. In doing so, a high concentration of chlorine exists inside the cell which can diffuse upstream and chemically attack heaters and other pool equipment. For this reason, a check valve is often used upstream of the chlorinator to prevent this backflow. A better solution is to simply have the chlorinator shut off 1 or 2 minutes before the pump—in this way, the salt cell has been flushed of the high concentration of chlorine and only normal pool water chlorine levels exist inside the cell—therefore no check valve is needed. Note that the volume of a salt cell is small compared to the volume of water flowing through it so only a few seconds of 'flushing' is needed after the cell shuts off.

The systems of the present disclosure could also include the ability to predict the need to shock or superchlorinate a pool or spa. Shocking or superchlorination of pool water is periodically required to oxidize bather waste. The system can anticipate the need to shock based on weather (e.g. sunlight, rainfall), bather load, turbidity, seasonality and combined chlorine level.

Additionally, in accordance with the present disclosure, the various UV/Ozone systems disclosed herein could also be modified to function as bromine generators. Bromine is commonly used in hot tubs because it does not form bromamines, unlike chlorine which forms malodorous chloramines. Bromine can be added to a hot tub by 1) bromine tablets, 2) by the generation of bromine using a salt bromine generator (starting with NaBr instead of NaCl as is done with chlorine) or 3) by generating the bromine in situ using ozone (a strong oxidizer) to convert bromide salt to bromine (Note: ozone will convert bromide to bromine. Bromides are introduced into hot tub as the NaBr salt). The hydroxyl radicals generated from a UV/Ozone system can be used to convert the bromides salt to bromine. The use of a UV/Ozone system not only regenerates bromine form the bromide ions but it reduces the amount of bromine needed to the overall sanitizing and oxidizing power of the UV/Ozone combination.

Still, further, in accordance with the present disclosure, pool lights or wall fittings can serve as turbidity and bather sensors. A pool light by definition is a transmitter of light. A pool light or wall sensor that contains a 'light receiver' can be calibrated using 'clear' water and the change in light intensity can be used to monitor the presence of bathers and/or changes in the turbidity of the water.

Having thus described the invention in detail, it is noted that the foregoing description is not intended to limit the spirit or scope of the present invention. Accordingly, what is desired to be protected by Letters Patent is set forth in the following claims.

What is claimed is:

1. A sensor, comprising:
   a body having a generally cylindrical outer wall and defining a chamber;
   a paddle wheel mounted within a recessed portion of the body, the paddle wheel in mechanical communication with a flow meter, the paddle wheel rotating when water flows past the sensor and the flow meter measuring a rate of water flow past the sensor when the paddle wheel rotates; and
   a plurality of electrodes extending from the body, the plurality of electrodes contacting water flowing past the sensor and measuring a concentration of salt present in, and conductivity of, the water,
   wherein the flow meter and the plurality of electrodes are in electrical communication with an electrical circuit.

2. The sensor of claim 1, wherein the plurality of electrodes measure a temperature of the water.

3. The sensor of claim 1, wherein the electrical circuit is potted in the chamber.

4. The sensor of claim 1, wherein the sensor is removably installed in an aperture of an electrolytic chlorinator and extends into a chamber of the electrolytic chlorinator, the paddle wheel aligned with water flowing past the flow sensor.

5. The sensor of claim 4, wherein operation of the electrolytic chlorinator is controlled based on one or more parameters measured by the sensor.

6. The sensor of claim 1, wherein the paddle wheel comprises magnets and rotary vanes, the magnets being positioned on ends of the rotary vanes and being detected by the electrical circuit in the chamber of the body.

7. The sensor of claim 6, wherein the paddle wheel is bidirectionally rotatable to detect water flow in two directions.

8. The sensor of claim 1, wherein the salt concentration measured by the sensor is compared to an impedance of plates of an electrolytic chlorinator in which the sensor is installed to determine a difference, and a condition of the electrolytic chlorinator is determined based on the difference.

9. A method for polarity reversal for an electrolytic chlorinator having a plurality of blades, comprising the steps of:
   applying a polarity to the blades of the electrolytic chlorinator for a first period of time;
   reversing the polarity of the blades of the electrolytic chlorinator for a second period of time;
   removing the polarity from the blades of the electrolytic chlorinator; and
   allowing a time delay to elapse before subsequent operation of the electrolytic chlorinator, the time delay sufficient to remove oxygen from pores and/or cracks in a surface of a cathode coating formed on the blades.

10. The method of claim 9, wherein the step of allowing the time delay to elapse reduces passivation of the cathode coating.

11. A sanitization system, comprising:
   an electrolytic chlorinator having a plurality of electrolytic plates for generating free chlorine from salt through electrolysis; and
   an integrated acid generator extending into a chamber of the electrolytic chlorinator and generating acid during operation of the electrolytic chlorinator.

12. The system of claim 11, wherein the integrated acid generator is removably positionable within the chamber of the electrolytic chlorinator through an aperture formed in the electrolytic chlorinator.

13. The system of claim 11, further comprising a power supply in electrical communication with the integrated acid generator for supplying electrical power to the integrated acid generator.

14. A sanitization system, comprising:
   an ultraviolet (UV) and/or ozone sterilization assembly; and
   a salt chlorine generator coupled to an output of the UV and/or ozone sterilization assembly, wherein the salt chlorine generator is positioned within the UV and/or ozone sterilization assembly.

15. The sanitization system of claim 14, further comprising an ozone injection system positioned at an input of the UV and/or ozone sterilization assembly for introducing ozone into water being supplied to the UV and/or ozone sterilization assembly.

16. The sanitization system of claim 14, further comprising a controller for controlling operation of the salt chlorine generator.

17. A sanitization system, comprising:
   a filter for filtering pool and/or spa water;
   an ultraviolet sanitization system positioned within the filter for sanitizing water within the filter; and
   an ozone feeder system positioned at an input of the filter for supplying ozone into water being supplied to the filter.

* * * * *